United States Patent
Hunter et al.

(10) Patent No.: US 11,946,058 B2
(45) Date of Patent: Apr. 2, 2024

(54) TARGETED CONTROL OF PESTS AND PATHOGENS BY PLANT DELIVERY OF 2′F-ANA-OLIGONUCLEOTIDES

(71) Applicants: The United States of America, as represented by the Secretary of Agriculture, Washington, DC (US); AUM LifeTech, Inc., Philadelphia, PA (US)

(72) Inventors: Wayne B. Hunter, Port St Lucie, FL (US); Veenu Aishwarya, Philadelphia, PA (US)

(73) Assignees: The United States of America, as represented by the Secretary of Agriculture, Washington, DC (US); AUM LifeTech, Inc., Philadelphia, PA (US)

( * ) Notice: Subject to any disclaimer, the term of this patent is extended or adjusted under 35 U.S.C. 154(b) by 0 days.

(21) Appl. No.: 17/568,884

(22) Filed: Jan. 5, 2022

(65) Prior Publication Data
US 2022/0119832 A1    Apr. 21, 2022

Related U.S. Application Data

(62) Division of application No. 16/502,236, filed on Jul. 3, 2019, now Pat. No. 11,254,945.

(60) Provisional application No. 62/694,512, filed on Jul. 6, 2018.

(51) Int. Cl.
*C12N 15/82* (2006.01)
*C12N 15/113* (2010.01)

(52) U.S. Cl.
CPC ........ *C12N 15/8218* (2013.01); *C12N 15/113* (2013.01); *C12N 2310/11* (2013.01); *C12N 2310/323* (2013.01); *C12N 2310/346* (2013.01)

(58) Field of Classification Search
CPC .................................................. C12N 15/8218
USPC ......................................................... 800/279
See application file for complete search history.

(56) References Cited

FOREIGN PATENT DOCUMENTS

WO      03064441      8/2003
WO      2018058006    3/2018

OTHER PUBLICATIONS

Dowler et al. Nucleic Acids Research 34:1669-1675 (Year: 2006).*
Hegaty et al. Appl. Microbiol. Biotechno. 102:1055-1065 (Year: 2018).*
Watts, J.K. et al., 2-Fluoro-4-ihioarabino-modified oligonucleotides: conformational switches linked to siRNA activity, Nucleic acids research, Feb. 6, 2007, pp. 1441-1451, vol. 38, No. 13.
Deleavey, G.F. et al., Synergistic effects between analogs of DNA and RNA improve the potency of siRNA-mediated gene silencing, Nucleic acids research, 2010, pp. 4547-4557, vol. 38, No. 13.
Kalota, A. et al., 2-Deoxy-2-fluroroB-d-arabinonucleic acid (2' F-ANA) modified oligonucleotides (ON) effect highly efficient, and persistent, gene silencing, Nucleic acids research, 2006, pp. 451-461, vol. 34, No. 2.
Thomas et al. The Plant Journal 25(4): 419-425 (Year: 2001).

* cited by examiner

*Primary Examiner* — Li Zheng
(74) *Attorney, Agent, or Firm* — John D. Fado; Mark D. McNemar

(57) ABSTRACT

Herein is disclosed synthetic oligonucleotides comprising 2′F-ANA nucleosides that can be utilized to control plant-chewing and phloem-feeding insects, bacteria present in such insects, and bacteria present in plants. The novel approaches and materials provided herein allow for reduction of pesticide and antibiotic use without the need to create genetically modified plants.

17 Claims, 21 Drawing Sheets
(3 of 21 Drawing Sheet(s) Filed in Color)
Specification includes a Sequence Listing.

```
                          SEQUENCE LISTING

<160> NUMBER OF SEQ ID NOS: 76

<210> SEQ ID NO 1
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 1
actgggatac gacaaggata t                                              21

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
tcttggaaca gcatagggac a                                              21

<210> SEQ ID NO 3
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 3
atatccttgt cgtatcccag t                                              21

<210> SEQ ID NO 4
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 4
cctcattatt cacaaggata g                                              21

<210> SEQ ID NO 5
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 5
tattgaaact gcttcggaag c                                              21

<210> SEQ ID NO 6
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 6
cgattaaacg cttgtccagc c                                              21
```

<210> SEQ ID NO 7
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 7
agatcctccg gcagcagaaa g                                        21

<210> SEQ ID NO 8
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 8
agcattggta gcggtatttc c                                        21

<210> SEQ ID NO 9
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 9
agcattggta gcggtatttc c                                        21

<210> SEQ ID NO 10
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 10
gaactcttat tcgagtacca g                                        21

<210> SEQ ID NO 11
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 11
gttgttaatt gaaggacaag g                                        21

<210> SEQ ID NO 12
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 12
acctatgcga ttaacgtgat t                                        21

<210> SEQ ID NO 13
<211> LENGTH: 21
<212> TYPE: DNA
<213> ORGANISM: Artificial Sequence
<220> FEATURE:
<223> OTHER INFORMATION: Chemically Synthesized

```
<400> SEQUENCE: 13
acctatgcaa taaatgtcat t                                              21

<210> SEQ ID NO 14
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 14
gattgaaggc cagggcaact t                                              21

<210> SEQ ID NO 15
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 15
ggcatggcga ccaacattcc g                                              21

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 16
tgttgacgga cacggcaact t                                              21

<210> SEQ ID NO 17
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 17
ggccgtgcga ttccggatct g                                              21

<210> SEQ ID NO 18
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 18
tatacctgat ttgcgagatg g                                              21

<210> SEQ ID NO 19
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 19
ttggtatgat gcagatgggc g                                              21

<210> SEQ ID NO 20
```

```
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 20
gaatggaata aaaaatatgt g                                              21

<210> SEQ ID NO 21
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 21
agaaagcagc gcattttctg c                                              21

<210> SEQ ID NO 22
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 22
ctcagagcgt gctaaatcag g                                              21

<210> SEQ ID NO 23
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 23
acaagcacta acatcctctc c                                              21

<210> SEQ ID NO 24
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 24
cctacacgaa tatcccttcc                                                20

<210> SEQ ID NO 25
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 25
tacaagcact aacatcctct c                                              21

<210> SEQ ID NO 26
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 26
```
aacaggttca agacgagcta c                                          21

<210> SEQ ID NO 27
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 27
ctatcctagt gaataatgat gc                                         22

<210> SEQ ID NO 28
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 28
gcatctgagg ctgtttccat a                                          21

<210> SEQ ID NO 29
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 29
cgattaaaag cttgtccagc c                                          21

<210> SEQ ID NO 30
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 30
tgtcctcgca tatacaaaat gg                                         22

<210> SEQ ID NO 31
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 31
ggccgtgcta tacctgattt g                                          21

<210> SEQ ID NO 32
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 32
gctatacctg atttgcgaga t                                          21

<210> SEQ ID NO 33
<211> LENGTH: 21
<212> TYPE: DNA

<213> ORGANISM: Artificial Sequence
<220> FEATURE:
<223> OTHER INFORMATION: Chemically Synthesized

<400> SEQUENCE: 33
ggtatggcga cgaatattcc c          21

<210> SEQ ID NO 34
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 34
gatcctccgg cagcggaaag g          21

<210> SEQ ID NO 35
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 35
gctatctttt gaagaaggag g          21

<210> SEQ ID NO 36
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 36
gatcctgtgc actgattaca g          21

<210> SEQ ID NO 37
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 37
ccattcttat tcctaagcca c          21

<210> SEQ ID NO 38
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 38
gatgatcttc tagtatttcg g          21

<210> SEQ ID NO 39
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 39
ggtttccatt ataatacctt g          21

```
<210> SEQ ID NO 40
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 40
gccatgtcca tgaacatgtc a                                             21

<210> SEQ ID NO 41
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 41
cgctaaaact attataagga t                                             21

<210> SEQ ID NO 42
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 42
atgtcggcat gtcgggcctc g                                             21

<210> SEQ ID NO 43
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 43
tacagcaagg agattctact a                                             21

<210> SEQ ID NO 44
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 44
tgggtactat tgccaaatct g                                             21

<210> SEQ ID NO 45
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 45
attcaccata ttcttcttgg c                                             21

<210> SEQ ID NO 46
<211> LENGTH: 21
<212> TYPE: DNA
<213> ORGANISM: Artificial Sequence
<220> FEATURE:
```

<223> OTHER INFORMATION: Chemically Synthesized

<400> SEQUENCE: 46
cataatacgc tccatattgg c                                              21

<210> SEQ ID NO 47
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 47
atatccttgt cgtatcccag t                                              21

<210> SEQ ID NO 48
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 48
cgcggggctc ttcgaccagt t                                              21

<210> SEQ ID NO 49
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 49
ggatcaggaa caatatccac g                                              21

<210> SEQ ID NO 50
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 50
ggctgtcggc tgccctcaca c                                              21

<210> SEQ ID NO 51
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 51
gaagaccaac atcctcatgg g                                              21

<210> SEQ ID NO 52
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 52
ggaacccgaa cacgcccatg t                                              21

```
<210> SEQ ID NO 53
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 53
gaagaccaac atcctgatgg g                                              21

<210> SEQ ID NO 54
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 54
ttcaagaaga ccaacatcct g                                              21

<210> SEQ ID NO 55
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 55
cgcggcggtg atgatttggg t                                              21

<210> SEQ ID NO 56
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 56
aacgtggtgg cgccgagacc g                                              21

<210> SEQ ID NO 57
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 57
tcaccctgtt tggagaatct g                                              21

<210> SEQ ID NO 58
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 58
ggacaaccca gagcgtgtta t                                              21

<210> SEQ ID NO 59
<211> LENGTH: 21
<212> TYPE: DNA
<213> ORGANISM: Artificial Sequence
<220> FEATURE:
<223> OTHER INFORMATION: Chemically Synthesized
```

```
<400> SEQUENCE: 59
ccatctgaca acatcgccaa g                                              21

<210> SEQ ID NO 60
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 60
ggtggccaca cagctgaagg g                                              21

<210> SEQ ID NO 61
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 61
cttagtccat catggcgccc c                                              21

<210> SEQ ID NO 62
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 62
ccaagtccaa ggctcgtatc c                                              21

<210> SEQ ID NO 63
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 63
gcccaaataa tggcccgcac c                                              21

<210> SEQ ID NO 64
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 64
gcgtagctag cagccattgg a                                              21

<210> SEQ ID NO 65
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 65
ggcccaggca ttagggtaat c                                              21

<210> SEQ ID NO 66
<211> LENGTH: 21
```

```
<212> TYPE: DNA
<213> ORGANISM: Artificial Sequence
<220> FEATURE:
<223> OTHER INFORMATION: Chemically Synthesized

<400> SEQUENCE: 66
aacgtggtgg cgccgagacc g                                              21

<210> SEQ ID NO 67
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 67
tgaaggatcg cattgaggtc ca                                             22

<210> SEQ ID NO 68
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 68
cagtttgaga tcgacaaacg a                                              21

<210> SEQ ID NO 69
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 69
cagtttgaga tcgacaaacg a                                              21

<210> SEQ ID NO 70
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 70
tgtccctatg ctgttccaag a                                              21

<210> SEQ ID NO 71
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 71
gcatcattat tcactaggat ag                                             22

<210> SEQ ID NO 72
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 72
```

```
tatggaaaca gcctcagatg c                                              21

<210> SEQ ID NO 73
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 73
cattttgtat atgcgaggac a                                              21

<210> SEQ ID NO 74
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 74
ttgtccagcc atatcaatag c                                              21

<210> SEQ ID NO 75
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 75
tagttccgat ttgtatgcat c                                              21

<210> SEQ ID NO 76
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 76
tgtatatgcg aggacatcgt c                                              21
```

TARGETED CONTROL OF PESTS AND PATHOGENS BY PLANT DELIVERY OF 2'F-ANA-OLIGONUCLEOTIDES

CROSS-REFERENCE

The present application is a divisional of U.S. patent application Ser. No. 16/502,236 Jul. 3, 2019 which claims priority to U.S. Provisional Patent Application Ser. No. 62/694,512 filed Jul. 6, 2018, the contents of which are expressly incorporated herein by reference.

BACKGROUND OF THE INVENTION

Background

Antisense oligonucleotides (ASOs) are short synthetic oligonucleotides that inhibit or modulate expression of a specific gene by Watson-Crick binding to cellular RNA targets. ASOs act through a number of different mechanisms. Some ASOs bind to an mRNA of a gene of interest, inhibiting expression either by blocking access (steric blocker) of the cellular translation machinery, or by inducing its enzymatic degradation (RNAse-H, RNAse-P). Alternatively, ASOs can target a complementary region of a specific pre-mRNA and modulate its splicing, typically to correct a dysfunctional protein.

Currently, more than 60 potential antisense drugs are under clinical investigation; however, there are very few agricultural reports on the uses of ASO to treat plants (Patel et al, Front. Microbiol., (2017) 8:687; Pietri et al, Insect Mol. Biol., (2014) 23:558-65; Cator et al, Sci. Rep. (2015) 5:11947). Plant pathogens, especially bacteria are extremely difficult to target. Few antibiotics are approved for crops and current attitudes towards the risk of antibiotic resistance development have prevented the expansion of antibiotics into crops to reduce bacterial pathogens. As such, the need exists to develop non-antibiotic compositions and methodologies to target such pathogens.

Emerging severe bacterial plant pathogens cause hundreds of millions of dollars of damage to crops annually. One such pathogen, *Candidatus Liberibacter asiaticus* (CLas) in citrus, is spread in the U.S. by the Asian citrus Psyllid, *Diaphorina citri* (*Hemiptera*: Liviidae). CLas bacterial infections result in citrus tree decline, lost yields, and tree death which threatens citrus production worldwide (de Graça & Korsten, (2004) "Citrus huanglongbing: review, present status and future strategies", p. 229-45, in Diseases of Fruits and Vegetables. Vol. 1 (N. Samh (ed.)); Bove, J., J. Plant Pathol. (2006) 88:7-37; Canales et al., PLoS ONE (2016) 11:e0146223). A closely related pathogen, *Candidatus Liberibacter solanacearum* (CLso) in Solanaceous crops, like potato and tomato, causes Zebra Chip disease (ZC) in potatoes (Hansen et al., Appl. Environ. Micro. (2008) 74:5862-5; Liefting et al., Plant Dis. (2008) 92:1474; Liefting et al., Plant Dis. (2009) 93:208-14; Munyaneza, J. E., Am. J. Pot. Res., (2012) 89:329-50) which has caused millions of dollars in losses in the U.S. The insect vector is the tomato/potato psyllid, *Bactericera cockerelli* (Šulc) (*Hemiptera*: Triozidae) (Munyaneza, J. E., supra).

Strains of *Xylella fastidiosa, Xf*, which are transmitted by many species of leafhoppers in the family Cicadellidae (*Hemiptera*) (e.g., the glassy-winged sharpshooter and blue-green sharpshooter), are associated with 'scorch-like" plant diseases, in fruit crops, grapevines, nuts, citrus, pears, peaches, and olives. In citrus a strain of *Xf* causes citrus variegated chlorosis (CVC), and has been linked to a sudden death pathotype. These strains of *Xf* can infect any type of citrus species, including hybrids. The severity of symptoms varies according to the genotype of the host with sweet oranges being the most susceptible, while grapefruit, lemons, limes mandarins, and trifoiates are only moderately susceptible (Garcia et al., Plant Dis. (2012) 96:1245-49; Gmitter et al., Tree Genet. Genomes (2012) 8:611-26; Casais et al., Pesquisa Agropecuaria Brasileira; (2014) 49:26-33; Fadel et al., Crop Protect. (2014) 64:115-21; Azevedo et al, Genetics Mol. Biol., (2016) 39:476-91). While CVC is not lethal in most cases, the infected trees always display reduced vigor, yield, and growth. Thus, infected trees have decreased productivity and lifespan (Garcia et al, supra).

While traditional treatment strategies (e.g., antibiotics) are being developed to address these concerns, there has been increasing problems associated with cost, registration, and public perception. Therefore, several roadblocks need to be solved. Products which can target internal pathogens of plants, or the endosymbionts of insect pests, could provide safer, highly specific treatments, if these were able to be more species-specific. Plants also depend upon their microbiota fauna to be healthy, thus treatments that may kill or reduce pathogens also needs to be safe for the beneficial host's microbes (Arora et al, BMC Biotechnol. (2015) 15:59). Herein, we provide RNA-targeting compositions and methodologies to meet these needs.

SUMMARY OF THE INVENTION

Provided in the present disclosure are multiple embodiments of the invention provided. In one embodiment, the disclosure provides an oligonucleotide comprising at least one 2'-deoxy-2'-fluoroarabinonucleotide (2'F-ANA)-modified nucleotide and at least one 2'-deoxyribonucleotide and having a sequence selected from the group consisting of SEQ ID NO: 1-76. In particular embodiments, the 2'F-ANA-modified nucleotides are positioned according to any of Formulas 1-16 (Table 2). In a specific embodiment, the 2'F-ANA-modified nucleotides are positioned according to Formula 6 (Table 2). In some embodiments, the 2'F-ANA-modified nucleotides comprise internucleotide linkages between nucleotides are phosphodiester bonds, phosphotriester bonds, phosphorothioate bonds (5'O—P(S)O-3O—, 5'S—P(O)O-3'-O—, and 5'O—P(O)O-3'S—), phosphorodithioate bonds, Rp-phosphorothioate bonds, Sp-phosphorothioate bonds, boranophosphate bonds, methylene bonds (methylimino), amide bonds(3'-$CH_2$—CO—NH-5' and 3'-$CH_2$—NH—CO-5'), methylphosphonate bonds, 3'-thioformacetal bonds, (3'S—$CH_2$—O5'), amide bonds (3'$CH_2$—C(O)NH-5'), phosphoramidate groups, or a combination thereof.

An additional embodiment provided herein is a method of inducing RNA silencing in a plant-chewing or phloem-feeding insect comprising the step of: a) providing an oligonucleotide comprising at least one 2'F-ANA-modified nucleotide and at least one 2'-deoxyribonucleotide and having the sequence of SEQ ID NO: 39-46, SEQ ID NO: 48-69 and SEQ ID NO: 71-76 to the insect in a manner whereby the insect to ingests the oligonucleotide, thereby inducing RNA silencing. In some embodiments, the 2'F-ANA-modified nucleotides are positioned according to any of Formula 1-16. In some embodiments, the insect ingests the oligonucleotide by consuming plant material containing the oligonucleotide. In additional embodiments of this methodology, the plant material comprises leaf tissue, root tissue, stem tissue, flower tissue, phloem, or a combination of these. In particular embodiments, the insect is *Diaphorina citri* or

*Diaprepes abbreviatus.* In other particular embodiments, the plant is a citrus plant, such as orange, lemon, clementine, lime, grapefruit, pomelo, citron, mandarin, and tangelo, or a potato plant. In some embodiments, this method has the additional step of applying the oligonucleotide to a plant, such as by soil applied root soak, injection, or foliar spray. In other embodiments, this method has the additional step of applying the oligonucleotide to an artificial diet, sugar solution or bait material.

Also provided herein is a method of controlling a plant-chewing or phloem-feeding insect, comprising the step of: providing an oligonucleotide comprising at least one 2'F-ANA-modified nucleotide and at least one 2'-deoxyribonucleotide and having a sequence selected from the group consisting of SEQ ID NO: 39-46, SEQ ID NO: 48-69 and SEQ ID NO: 71-76 in a manner whereby the insect to ingests the oligonucleotide, thereby inducing RNA silencing and a detrimental effect to the insect. In some embodiments, the 2'F-ANA-modified nucleotides are positioned according to any of Formulas 1-16. In some embodiments, the detrimental effect is increased mortality compared to insects not exposed to the oligonucleotide. In particular embodiments, the insect is *Diaphorina citri* or *Diaprepes abbreviatus*. In other particular embodiments, the plant is a citrus plant. In particular embodiments, the oligonucleotide is applied to a plant, such as by root soak, injection or foliar spray. In another embodiment, the oligonucleotide is applied to an artificial diet, sugar solution or bait material.

The present disclosure also provides a method of controlling bacteria present in an insect comprising the steps of: a) contacting a food source edible by the insect with an oligonucleotide comprising at least one 2'F-ANA-modified nucleotide and at least one 2'-deoxyribonucleotide that targets a mRNA present in the bacteria; b) allowing the insect to feed on the food source, thereby ingesting the oligonucleotide; and c) inducing RNA silencing in at least some of the bacteria present in the insect, thereby controlling the bacteria. In particular embodiments, the oligonucleotide is one or more of SEQ ID NO: 4-38. In some embodiments, the 2'F-ANA-modified nucleotides are positioned according to any of Formulas 1-16. In specific embodiments, the bacteria is *Candidatus Liberibacter asiaticus* or *Candidatus Liberibacter solanacearum*. In some embodiments of this method, the food source is a plant, a bait material, an artificial diet, or a sugar solution. In some embodiments, the food source is a plant, such as a citrus plant, and the oligonucleotide is contacted with the plant by root soak, injection or foliar spray. In specific embodiments, the insect is *Diaphorina citri* or *Diaprepes abbreviatus*.

Also provided in the present disclosure is a method of controlling a bacterium, wherein the bacterium is a plant pathogen present in plant tissues, comprising the steps of: a) contacting the plant with an oligonucleotide having at least one 2'F-ANA-modified nucleotide and at least one 2'-deoxyribonucleotide in a manner whereby the oligonucleotide to distributes through at least some of the plant tissues, thereby providing the oligonucleotide to the bacterium; and b) inducing RNA silencing in the bacterium, thereby inducing a detrimental effect to the bacterium. In specific embodiments of this method, the oligonucleotide has the sequence of one or more of SEQ ID NO: 4-38. In some embodiments, the 2'F-ANA-modified nucleotides are positioned according to any of Formulas 1-16. In specific embodiments, the bacterium is *Candidatus Liberibacter asiaticus* or *Candidatus Liberibacter solanacearum*. In some embodiments, the oligonucleotide is contacted with the plant, such as a citrus or potato plant, by root soak, injection or foliar spray.

The present disclosure also provides a method of inducing RNA silencing in a *Diaphorina citri* or *Diaprepes abbreviatus* insect comprising the step of: contacting *D. citri* or *D. abbreviatus* with an oligonucleotide having at least one 2'F-ANA-modified nucleotide and at least one 2'-deoxyribonucleotide in an amount sufficient to induce RNA silencing. In particular embodiments, the oligonucleotide is one or more of SEQ ID NO: 39-46, SEQ ID NO: 48-69 and SEQ ID NO: 71-76. In particular embodiments, the 2'F-ANA-modified nucleotides are positioned according to any of Formulas 1-16. In a specific embodiment, the insect is *D. citri* and the contacting comprises ingestion of phloem of a plant, wherein the phloem comprises the oligonucleotide. In another specific embodiment, the insect is *D. abbreviatus* and the contacting comprises consumption of plant tissue, wherein the plant tissue comprises the oligonucleotide.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

Figure 1:
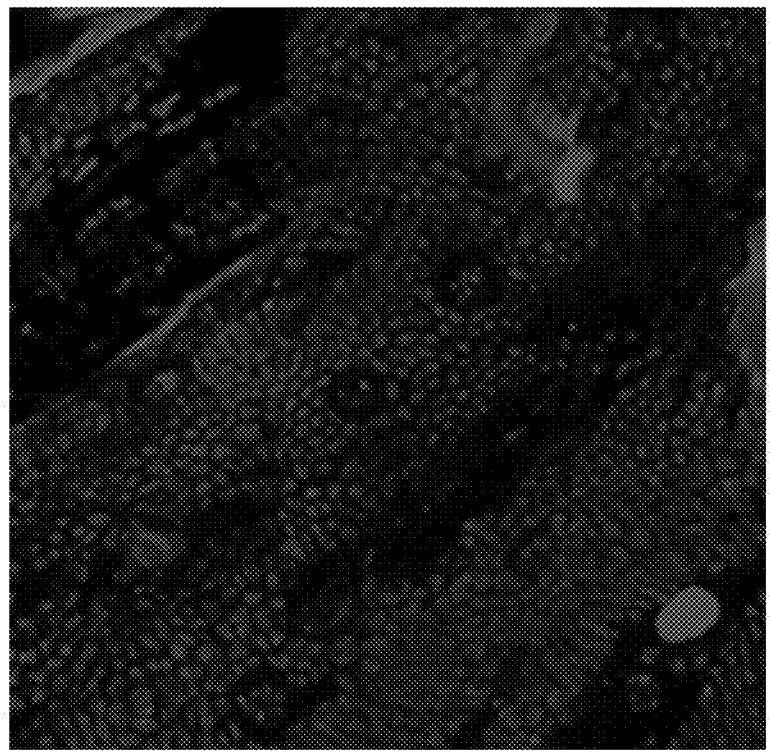
FIG. 1 provides an image from a confocal microscopy deep scan through a citrus leaf from a cutting which absorbed red fluorescently labeled 2'F-ANA oligonucleotide (F-ASO) (the F-ASO was a scrambled control or "SC-ASO"), at approximately 12-micron steps through leaf of treated citrus cutting, approx. 5 cm long, new growth, absorbed the SC-ASO, labeled with fluorophore.

FIG. 9 provides a representation of data showing changes in branch diameter between control (untreated) CLas-infected trees and trees receiving an anti-CLas F-ASO. Data shown is from "Branch A".

FIG. 10 provides a representation of data showing changes in branch diameter between control (untreated) CLas-infected trees and trees receiving an anti-CLas F-ASO. Data shown is from "Branch B".

FIG. 11 provides a representation of data showing changes in CLso-symptom severity scores in control (untreated) CLso-infected potato plants and plants receiving various F-ASOs targeting CLso DnaB helicase transcript.

FIG. 12 provides a representation of data showing symptom progression in CLso-infected potato plants (foliar disease) over a 30-day period.

FIG. 13 provides a representation of data showing changes in CLso titers in control (untreated) CLso-infected potato plants and plants receiving various F-ASOs targeting CLso DNA gyrase subunit A.

FIG. 14 provides a representation of data showing a comparison of potato plant growth between uninfected (CLso-free) controls, CLso-infected controls, and plants treated with various F-ASOs targeting DNA gyrase subunit A.

FIG. 15 provides a representation of data showing changes in CLas bacteria copy number in CLas-carrying psyllids receiving a F-ASO targeting CLas DNA B Helicase via feeding on citrus leaf tissue containing the F-ASO.

FIG. 16 provides a representation of data showing changes in CLas bacteria copy number in CLas-carrying psyllids receiving various F-ASOs targeting CLas DNA B Helicase following ingestion of the F-ASOs by feeding on treated citrus leaf tissue.

FIG. 17 provides a representation of data showing changes in CLas bacteria copy number in CLas-carrying psyllids receiving F-ASOs targeting CLas acetyl-CoA carboxylase biotin carboxylase subunit.

FIG. 18 provides a representation of data showing changes in CLas bacteria copy number in CLas-carrying psyllids receiving individual F-ASOs targeting CLas DNA Ligase-A.

FIG. 19 provides a representation of data showing mortality effects on *D. abbreviatus* following ingestion of a mixture of F-ASOs targeting *D. abbreviatus* syntaxin 1A transcript.

FIG. 20 provides a representation of data showing mortality effects on *D. citri* following ingestion of individual F-ASOs targeting *D. abbreviatus* heat shock protein 90 transcript.

FIG. 21 provides a representation of data showing mortality effects on *D. citri* following ingestion of individual F-ASOs targeting various *D. citri* transcripts.

DETAILED DESCRIPTION OF THE INVENTION

In agricultural food production, some antibiotics have been commonly used to prevent infections in animals and plants and chemicals are used insecticides, antimicrobials and herbicides. Long-term and widespread use of these traditional methods leads to several common concerns, including drug-resistant bacteria, undesirable effects on beneficial species, and environmental impact. An alternative presented herein are ASOs, which are synthetic single-stranded DNA molecules synthesized to increase binding affinity to genetic targets and containing modifications to naturally occurring nucleic acids. The use of ASOs provides several strategies to modulate RNA and protein production across both eukaryotes and prokaryotes and have the potential to increase the effectiveness of biological control agents in the field, because of their high specificity for genetic targets.

Antisense oligonucleotides of the present invention are single-stranded deoxyribonucleotides complementary to a targeted mRNA. Hybridization of an ASO to its target mRNA via Watson-Crick base pairing can result in specific inhibition of gene expression by various mechanisms, depending on the chemical make-up of the ASO and location of hybridization, resulting in reduced levels of translation of the target transcript (Crooke 2004). ASOs of the present invention typically encompass oligonucleotides having at least one sugar-modified nucleoside (e.g., 2'F-ANA) as well as naturally-occurring 2'-deoxy-nucleosides (see, e.g., U.S. Pat. No. 8,278,103 which is specifically incorporated by reference). ASO-induced protein knockdown is usually achieved by induction of RNase H endonuclease activity. When activated, the RNAse H cleaves the RNA-DNA heteroduplex leading to the degradation of the target mRNA. This leaves the ASO intact so that it can function again (Wu et al, J. Biol. Chem. (2004) 279:181-9).

As provided herein, we show that ASOs can be utilized by environmental application (e.g., root soak, foliar spray) to plants in horticultural and agricultural settings. ASOs solve the problems encountered with topically applied nucleotide-based strategies (e.g., dsRNA) which are subject to environmental degradation. The ASO technology provides greater stability due to modifications of the backbone of the single-stranded RNA/DNA hybrid molecule, and increases resistance to degradation by using synthetic nucleotides in the structure (Wilds & Damha, Nucl. Acids Res. (2000) 28:3625-35; Dias and Stein, Mol. Canc. Ther. (2002) 1:347-55; Chan et al, Clin. Exp. Pharmacol. Physiol., (2006) 33:533-40).

While there are many types of ASO's, the main discoveries in ASO development leading to use in therapies in 1998 included two main chemical modifications. These set the foundation for the starting point for ASO construction and design of novel ASO's (Chan et al, supra; Martin-Pintado, et al, Angew. Chem. Int. Ed. Engl. (2012) 52:12065-68; Lundin et al, Human Gene Ther., (2015) 26:475-85). These modifications include the 2'-fluoro (2'-F) substitutions and the phosphorothioate chemistry (Noronha et al, Biochem. (2000) 39:7050-62; Watts & Damha, Can. J. Chem. (2008) 86:641-56; Neef & Luedtke, Proc. Natl. Acad. Sci. USA (2011) 108:20404-9). These two modifications constitute synthetic analogs of naturally occurring nucleic acids, but which have greater stability and activity (Ludin et al, supra). Thus, some embodiments of the present invention use 2'-F substitutions (Reist et al, J. Org. Chem., (1964) 29:554-8; Codington et al, J. Org. Chem. (1964) 29:558-64), and modification of the sugar backbone with phosphorotioate chemistry (Eckstein, F., J. Am. Chem. Soc. (1966) 88:4292-94) to produce ASOs containing 2'-deoxy-2'-fluoro-β-D-arabinonucleic acid (2'F-ANA), termed "FANA antisense oligonucleotides" (F-ASO). The stability, specificity and non-toxicity of F-ASO oligonucleotides make them good candidates for difficult to control pathogens involving microbes and insects.

As detailed further herein, we demonstrate that F-ASO can be applied to plants as topical spray applications to foliage, soils, or in baits and results in suppression of RNA targets in bacterial pathogens of plants and the endosymbionts in arthropods that feed on treated plants or baits. These results demonstrate that for chewing insect pests, topical applications of ASO are effective in targeting Lepidoptera and Coleoptera pests. As for plant-feeding hemipterans, like sap-sucking insects—psyllids, aphids, leafhoppers, whitefly, planthoppers and others—the F-ASOs are delivered into, and move systemically through the vascular tissues of plants allowing for these insects to ingest the F-ASO when they feed. Our results demonstrate that, similarly to other small nucleic acids that are topically applied to foliage as a spray, or the soil root zone of plants, the F-ASOs of the present invention are absorbed through leaves and roots and then move systemically throughout the plant within hours (Andrade & Hunter (I), (2016) "RNA Interference—Natural Gene-Based Technology for Highly Specific Pest Control (HiSPeC)", p. 391-409. in RNA Interference (I. Y. Abdurakhmonov (ed.); Andrade & Hunter (II), Entomol. Exper. Appl., (2017) 162:389-96; Hunter et al, Southwest. Entomol., (2012) 37:85-7; Ivashuta et al, RNA, (2015) 21:840-50; Li et al, Plant Cell Environ., (2015) 38:2277-85; Joga et al, Front. Physiol., (2016) 7:553).

Herein, we demonstrate that plant delivered strategies, using exogenously-applied F-ASO works for diverse plant species (citrus, grapevines, woody ornamentals, sunflowers, basil, okra) and insects from several arthropod Orders: *Hemiptera*, Coleoptera, Lepidoptera, Diptera. Together, this data indicates that the novel approaches described herein can be utilized to target many Arthropods and that a wide variety of plants are broadly amenable to the novel treatment methodologies with ASO products described herein.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art.

Any suitable materials and/or methods known to those of skill can be utilized in carrying out the instant invention. Materials and/or methods for practicing the instant invention are described. Materials, reagents, and the like to which reference is made in the following description and examples are obtainable from commercial sources, unless otherwise noted.

As used in the specification and claims, use of the singular "a", "an", and "the" include plural references unless the context clearly dictates otherwise.

The terms "isolated", "purified", or "biologically pure" as used herein, refer to material that is substantially or essentially free from components that normally accompany the referenced material in its native state.

The terms "about" and "approximately" are defined as plus or minus ten percent of a recited value. For example, about 1.0 g means 0.9 g to 1.1 g and all values within that range, whether specifically stated or not.

"Citrus" as used herein refers to any species of tree producing any variety of citrus fruit, such as oranges, tangerines, clementines, lemons, limes, and the like.

For the purpose of the invention, the "complement of a nucleotide sequence X" is the nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A< >T; G< >C; A< >U) and reading in the 5' to 3' direction, i.e., in opposite direction of the represented nucleotide sequence. In the context of the present disclosure, this term also includes synthetic analogs of DNA/RNA (e.g., 2'F-ANA oligos).

The term "control", and grammatical variants thereof, is utilized in several contexts herein. Within experiments, a "control" is a means by which experimental variables are tested to eliminate as a cause of observed results. With regards to diseases (e.g., citrus greening), the term "control" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment. With regards to organisms (e.g., insects, bacteria, etc.), the term "control" as used herein refers to any means for preventing infection or infestation, reducing the population of already infected areas, or elimination of population(s) whose "control" is desired. Indeed, "controlling" as used herein refers to any indicia of success in prevention, elimination, reduction, repulsion, or amelioration of a target population or a problem caused by the target population (e.g., insect pest, microbe, etc).

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

"Insect" or "insect pest" as used herein means any variety of insects that may cause harm to plants, trees, fruits, or nuts or products produced thereby or therefrom. In exemplary embodiments, such pests include leaf-eating and sap-feeding arthropods, such as the Asian citrus psyllid.

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seeds (including embryo, endosperm, and seed coat) and fruit (the mature ovary), plant tissue (e.g., vascular tissue, ground tissue, and the like) and cells (e.g., guard cells, egg cells, trichomes and the like).

As used herein, "preventing" a disease refers to inhibiting the full development of a disease.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman & Wunsch, J. Mol. Biol., (1970) 48:3, 443-53). A computer-assisted sequence alignment can be conveniently performed using a standard software program such as GAP which is part of the Wisconsin Package Version 10.1 (Genetics Computer Group, Madison, Wisconsin, USA) using the default scoring matrix with a gap creation penalty of 50 and a gap extension penalty of 3.

FANA Antisense Oligonucleotides

The chemistry and construction of 2'F-ANA oligonucleotides (also termed FANA or F-ASO) has been described elsewhere in detail (See, e.g., U.S. Pat. Nos. 8,278,103 and 9,902,953, each of which is specifically incorporated herein in their entirety by reference). The F-ASOs and methods of using them disclosed herein contemplate any FANA chemistries known in the art. In some embodiments, a F-ASO comprises an internucleoside linkage comprising a phosphate, thereby being an oligonucleotide. In some embodiments, the sugar-modified nucleosides and/or 2'-deoxynucleosides comprise a phosphate, thereby being sugar-modified nucleotides and/or 2'-deoxynucleotides. In some embodiments, a F-ASO comprises an internucleoside linkage comprising a phosphorothioate. In some embodiments, the internucleoside linkage is selected from phosphorothioate, phosphorodithioate, methylphosphorothioate, Rp-phosphorothioate, Sp-phosphorothioate. In some embodiments, the a F-ASO comprises one or more internucleotide linkages selected from the group consisting of: (a) phosphodiester; (b) phosphotriester; (c) phosphorothioate; (d) phosphorodithioate; (e) Rp-phosphorothioate; (f) Sp-phosphorothioate; (g) boranophosphate; (h) methylene (methylimino) (3'CH$_2$—N(CH$_3$)—O5'); (i) 3'-thioformacetal (3'S—CH$_2$—O5'); (j) amide (3'CH$_2$—C(O)NH-5'); (k) methylphosphonate; (l) phosphoramidate (3'-OP(O$_2$)—N5'); and (m) any combination of (a) to (l).

In some embodiments, F-ASOs comprising alternating segments or units of sugar-modified nucleotides (e.g., arabinonucleotide analogues [e.g., 2'F-ANA]) and 2'-deoxyribonucleotides (DNA) are utilized. In some embodiments, a F-ASO disclosed herein comprises at least 2 of each of sugar-modified nucleotide and 2'-deoxynucleotide segments, thereby having at least 4 alternating segments overall. Each alternating segment or unit may independently contain 1 or a plurality of nucleotides. In some embodiments, each alternating segment or unit may independently contain 1 or 2 nucleotides. In some embodiments, the segments each comprise 1 nucleotide. In some embodiments, the segments each comprise 2 nucleotides. In some embodiments, the plurality of nucleotides may consist of 2, 3, 4, 5 or 6 nucleotides. A F-ASO may contain an odd or even number of alternating segments or units and may commence and/or terminate with a segment containing sugar-modified nucleotide residues or DNA residues. Thus, a F-ASO may be represented as follows:

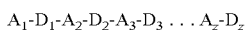

Where each of A$_1$, A$_2$, etc. represents a unit of one or more (e.g., 1 or 2) sugar-modified nucleotide residues (e.g., 2'F-ANA) and each of D$_1$, D$_2$, etc. represents a unit of one or more (e.g., 1 or 2) DNA residues. The number of residues within each unit may be the same or variable from one unit to another. The oligonucleotide may have an odd or an even number of units. The oligonucleotide may start (i.e. at its 5' end) with either a sugar-modified nucleotide-containing unit (e.g., a 2'F-ANA-containing unit) or a DNA-containing unit. The oligonucleotide may terminate (i.e. at its 3' end) with either a sugar-modified nucleotide-containing unit or a DNA-containing unit. The total number of units may be as few as 4 (i.e. at least 2 of each type).

In some embodiments, a F-ASO disclosed herein comprises alternating segments or units of arabinonucleotides and 2'-deoxynucleotides, wherein the segments or units each independently comprise at least one arabinonucleotide or 2'-deoxynucleotide, respectively. In some embodiments, the segments each independently comprise 1 to 2 arabinonucleotides or 2'-deoxynucleotides. In some embodiments, the segments each independently comprise 2 to 5 or 3 to 4 arabinonucleotides or 2'-deoxynucleotides. In some embodiments, a F-ASO disclosed herein comprises alternating segments or units of arabinonucleotides and 2'-deoxynucleotides, wherein the segments or units each comprise one arabinonucleotide or 2'-deoxynucleotide, respectively. In some embodiments, the segments each independently comprise about 3 arabinonucleotides or 2'-deoxynucleotides. In some embodiments, a F-ASO disclosed herein comprises alternating segments or units of arabinonucleotides and 2'-deoxynucleotides, wherein the segments or units each comprise one arabinonucleotide or 2'-deoxynucleotide, respectively. In some embodiments, a F-ASO disclosed herein comprises alternating segments or units of arabinonucleotides and 2'-deoxynucleotides, wherein said segments or units each comprise two arabinonucleotides or 2'-deoxynucleotides, respectively.

In some embodiments, a F-ASO disclosed herein has a structure selected from the group consisting of:

| a) | $(A_x\text{-}D_y)_n$ | I |
|---|---|---|
| b) | $(D_y\text{-}A_x)_n$ | II |
| c) | $(A_x\text{-}D_y)_m\text{-}A_x\text{-}D_y\text{-}A_x$ | III |
| d) | $(D_y\text{-}A_x)_m\text{-}D_y\text{-}A_x\text{-}D_y$ | IV | wherein each of m, x and y are each independently an integer greater than or equal to 1, n is an integer greater than or equal to 2, A is a sugar-modified nucleotide and D is a 2'-deoxyribonucleotide. For example, a F-ASO disclosed herein has structure I wherein x=1, y=1 and n=10, thereby having a structure:

In another example, a F-ASO disclosed herein has structure II wherein x=1, y=1 and n=10, thereby having a structure:

In another example, a F-ASO disclosed herein has structure III wherein x=1, y=1 and n=9, thereby having a structure:

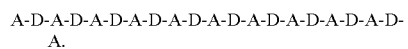

In another example, a F-ASO disclosed herein has structure IV wherein x=1, y=1 and n=9, thereby having a structure:

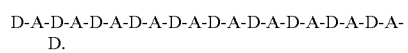

In another example, a F-ASO disclosed herein has structure I wherein x=2, y=2 and n=5, thereby having a structure:

In another example, a F-ASO disclosed herein has structure II wherein x=2, y=2 and n=5, thereby having a structure:

D-D-A-A-D-D-A-A-D-D-A-A-D-D-A-A-D-D-A-A.

In another example, a F-ASO disclosed herein has structure III wherein x=2, y=2 and m=4, thereby having a structure:

A-A-D-D-A-A-D-D-A-A-D-D-A-A-D-D-A-A-D-D-A-A.

In another example, a F-ASO disclosed herein has structure IV wherein x=2, y=2 and m=4, thereby having a structure:

D-D-A-A-D-D-A-A-D-D-A-A-D-D-A-A-D-D-A-A-D-D.

Specific examples of modified synthetic F-ASOs described herein include the F-ASOs shown in Table 1 below:

TABLE 1

Exemplary 2'F-ANA oligonucleotides

| Descriptor | Sequence | SEQ ID NO: |
|---|---|---|
| SC-ASO-1 | ACTGGGATACGACAAGGATAT | SEQ ID NO: 1 |
| SC-ASO-2 | TCTTGGAACAGCATAGGGACA | SEQ ID NO: 2 |
| SC-ASO-3 | ATATCCTTGTCGTATCCCAGT | SEQ ID NO: 3 |
| CLASDNAB-1 | CCTCATTATTCACAAGGATAG | SEQ ID NO: 4 |
| CLASDNAB-2 | TATTGAAACTGCTTCGGAAGC | SEQ ID NO: 5 |
| CLASDNAB-3 | CGATTAAACGCTTGTCCAGCC | SEQ ID NO: 6 |
| CLASDNAB-4 | CACTTTGTATAAGCAAGAATA | SEQ ID NO: 7 |
| Las-GYR2 | AGATCCTCCGGCAGCAGAAAG | SEQ ID NO: 8 |
| Las-GYR3 | AGCATTGGTAGCGGTATTTCC | SEQ ID NO: 9 |
| Las-GYR4 | GAACTCTTATTCGAGTACCAG | SEQ ID NO: 10 |
| Las-GYRA5 | GTTGTTAATTGAAGGACAAGG | SEQ ID NO: 11 |
| Las-GYRA6 | ACCTATGCGATTAACGTGATT | SEQ ID NO: 12 |
| Las-GYRA7 | ACCTATGCAATAAATGTCATT | SEQ ID NO: 13 |
| Las-GYRA8 | GATTGAAGGCCAGGGCAACTT | SEQ ID NO: 14 |
| Las-GYRA9 | GGCATGGCGACCAACATTCCG | SEQ ID NO: 15 |
| Las-GYRA10 | TGTTGACGGACACGGCAACTT | SEQ ID NO: 16 |
| Las-GYRA11 | GGCCGTGCGATTCCGGATCTG | SEQ ID NO: 17 |
| Las-GYR12 | TATACCTGATTTGCGAGATGG | SEQ ID NO: 18 |
| Las-GYR13 | TTGGTATGATGCAGATGGGCG | SEQ ID NO: 19 |
| Las-GYR14 | GAATGGAATAAAAAATATGTG | SEQ ID NO: 20 |
| Las-GYR15 | AGAAAGCAGCGCATTTTCTGC | SEQ ID NO: 21 |
| CLIBASIA-1 | CTCAGAGCGTGCTAAATCAGG | SEQ ID NO: 22 |
| CLIBASIA-2 | ACAAGCACTAACATCCTCTCC | SEQ ID NO: 23 |
| CLIBASIA-3 | CCTACACGAATATCCCTTCC | SEQ ID NO: 24 |
| CLIBASIA-4 | TACAAGCACTAACATCCTCTC | SEQ ID NO: 25 |
| CLIBASIA-5 | AACAGGTTCAAGACGAGCTAC | SEQ ID NO: 26 |

TABLE 1-continued

Exemplary 2'F-ANA oligonucleotides

| Descriptor | Sequence | SEQ ID NO: |
|---|---|---|
| CLsoDNAB-1 | CTATCCTAGTGAATAATGATGC | SEQ ID NO: 27 |
| CLsoDNAB-2 | GCATCTGAGGCTGTTTCCATA | SEQ ID NO: 28 |
| CLso-DNAB-3 | CGATTAAAAGCTTGTCCAGCC | SEQ ID NO: 29 |
| CLsoDNAB-4 | TGTCCTCGCATATACAAAATGG | SEQ ID NO: 30 |
| CLsoGYR-2 | GGCCGTGCTATACCTGATTTG | SEQ ID NO: 31 |
| CLsoGYR-3 | GCTATACCTGATTTGCGAGAT | SEQ ID NO: 32 |
| CLsoGYR-4 | GGTATGGCGACGAATATTCCC | SEQ ID NO: 33 |
| CLsoGYR-5 | GATCCTCCGGCAGCGGAAAGG | SEQ ID NO: 34 |
| CLASBTIN_1 | GCTATCTTTTGAAGAAGGAGG | SEQ ID NO: 35 |
| CLASBTIN_2 | GATCCTGTGCACTGATTACAG | SEQ ID NO: 36 |
| CLASBTIN_3 | CCATTCTTATTCCTAAGCCAC | SEQ ID NO: 37 |
| CLASBTIN_4 | GATGATCTTCTAGTATTTCGG | SEQ ID NO: 38 |
| C1-DRW-1 | GGTTTCCATTATAATACCTTG | SEQ ID NO: 39 |
| C1-DRW-2 | GCCATGTCCATGAACATGTCA | SEQ ID NO: 40 |
| C1-DRW-3 | CGCTAAAACTATTATAAGGAT | SEQ ID NO: 41 |
| C1-DRW-4 | ATGTCGGCATGTCGGGCCTCG | SEQ ID NO: 42 |
| Da90-1 | TACAGCAAGGAGATTCTACTA | SEQ ID NO: 43 |
| Da90-2 | TGGGTACTATTGCCAAATCTG | SEQ ID NO: 44 |
| Da90-3 | ATTCACCATATTCTTCTTGGC | SEQ ID NO: 45 |
| Da90-4 | CATAATACGCTCCATATTGGC | SEQ ID NO: 46 |
| C1-SC-1 | ATATCCTTGTCGTATCCCAGT | SEQ ID NO: 47 |
| DBac-1 | CGCGGGGCTCTTCGACCAGTT | SEQ ID NO: 48 |
| DBac-2 | GGATCAGGAACAATATCCACG | SEQ ID NO: 49 |
| DBac-3 | GGCTGTCGGCTGCCCTCACAC | SEQ ID NO: 50 |
| DBac-4 | GAAGACCAACATCCTCATGGG | SEQ ID NO: 51 |
| DBac-5 | GGAACCCGAACACGCCCATGT | SEQ ID NO: 52 |
| DCACE-1 | GAAGACCAACATCCTGATGGG | SEQ ID NO: 53 |
| DCACE-2 | TTCAAGAAGACCAACATCCTG | SEQ ID NO: 54 |
| DCACE-3 | CGCGGCGGTGATGATTTGGGT | SEQ ID NO: 55 |
| DCACE-4 | AACGTGGTGGCGCCGAGACCG | SEQ ID NO: 56 |
| DCACE-5 | TCACCCTGTTTGGAGAATCTG | SEQ ID NO: 57 |
| DCACE-6 | GGACAACCCAGAGCGTGTTAT | SEQ ID NO: 58 |
| DC60-1 | CCATCTGACAACATCGCCAAG | SEQ ID NO: 59 |
| DC60-2 | GGTGGCCACACAGCTGAAGGG | SEQ ID NO: 60 |
| DC60-3 | CTTAGTCCATCATGGCGCCCC | SEQ ID NO: 61 |
| DC60-4 | CCAAGTCCAAGGCTCGTATCC | SEQ ID NO: 62 |
| DcTR-1 | GCCCAAATAATGGCCCGCACC | SEQ ID NO: 63 |
| DcTR-2 | GCGTAGCTAGCAGCCATTGGA | SEQ ID NO: 64 |

TABLE 1-continued

Exemplary 2'F-ANA oligonucleotides

| Descriptor | Sequence | SEQ ID NO: |
|---|---|---|
| DcTR-3 | GGCCCAGGCATTAGGGTAATC | SEQ ID NO: 65 |
| DcTR-4 | AACGTGGTGGCGCCGAGACCG | SEQ ID NO: 66 |
| DcTR-5 | TGAAGGATCGCATTGAGGTCCA | SEQ ID NO: 67 |
| DcTR-7 | CAGTTTGAGATCGACAAACGA | SEQ ID NO: 68 |
| DcTR-8 | CAGTTTGAGATCGACAAACGA | SEQ ID NO: 69 |
| C1-SC-2 Fluor | TGTCCCTATGCTGTTCCAAGA | SEQ ID NO: 70 |
| CLsoDNAB-5 | GCATCATTATTCACTAGGATAG | SEQ ID NO: 71 |
| CLsoDNAB-6 | TATGGAAACAGCCTCAGATGC | SEQ ID NO: 72 |
| CLsoDNAB-7 | CATTTTGTATATGCGAGGACA | SEQ ID NO: 73 |
| CLsoDNAB-8 | TTGTCCAGCCATATCAATAGC | SEQ ID NO: 74 |
| CLsoDNAB-9 | TAGTTCCGATTTGTATGCATC | SEQ ID NO: 75 |
| CLsoDNAB-10 | TGTATATGCGAGGACATCGTC | SEQ ID NO: 76 |

The formulas shown in Table 2 may be applied to any of SEQ ID Nos: 1-70, or a portion thereof, wherein X represents a nucleotide (A, C, G, T, or U), and wherein bold and underlined nucleotides represent sugar-modified or 2'F-ANA-modified nucleotide and with backbone phosphorothioate linkages.

TABLE 2

Exemplary 2'F-ANA nucleoside placement within 21-mer F-ASOs

| 21 nucleotides | Formula |
|---|---|
| Formula 1 | XXXXXXXXXXXXXXXXXXXXX |
| Formula 2 | XXXXXXXXXXXXXXXXXXXXX |
| Formula 3 | XXXXXXXXXXXXXXXXXXXXX |
| Formula 4 | XXXXXXXXXXXXXXXXXXXXXXX |
| Formula 5 | XXXXXXXXXXXXXXXXXXXXXX |
| Formula 6 | XXXXXXXXXXXXXXXXXXXXX |
| Formula 7 | XXXXXXXXXXXXXXXXXXXXX |
| Formula 8 | XXXXXXXXXXXXXXXXXXXXX |
| Formula 9 | XXXXXXXXXXXXXXXXXXXXX |
| Formula 10 | XXXXXXXXXXXXXXXXXXXXX |
| Formula 11 | XXXXXXXXXXXXXXXXXXXXX |
| Formula 12 | XXXXXXXXXXXXXXXXXXXXXXX |
| Formula 13 | XXXXXXXXXXXXXXXXXXXXXXX |
| Formula 14 | XXXXXXXXXXXXXXXXXXXXX |
| Formula 15 | XXXXXXXXXXXXXXXXXXXX |
| Formula 16 | XXXXXXXXXXXXXXXXXXXXX |

F-ASO Compositions

In particular embodiments, the present invention provides a composition having an inhibitory F-ASO represented by one or more of SEQ ID NOs. 1-70 and having 2'F-ANA placement within the F-ASO as shown in any of Formulas 1-16 (Table 2) and specific for a target mRNA or fragment thereof. Other placements of 2'F-ANA oligonucleosides within a F-ASO are also contemplated, as are F-ASOs of 10, 11, 12, 13, 14, 15, 16, 17, 18, 19, 20, 21, 22, 23, 24, 25, 26, 27, 28, 29, 30, or more bases in length. Typically, F-ASOs of the present invention are provided to a target recipient (e.g., plant, insect or bacteria) in an amount sufficient to induce RNA silencing, thereby inhibiting production of the polypeptide encoded by one or more of the full-length genes targeted by SEQ ID NOs. 1-70. For example, a F-ASO of the present invention is applied to a plant topically, allowing for uptake of the F-ASO by the plant. The F-ASO can control a bacterial pathogen currently infecting the plant. Additionally, when a plant pest (e.g., D. citri) is feeding on a treated plant, the insect can ingest a sufficient level of the F-ASO to control or kill bacteria harbored by the insect pest and/or control or kill the insect pest itself.

In addition to a F-ASO of the present invention, compositions of the present invention intended to be applied to a plant can be formulated so as to contain one or more phagostimulants, pesticides, fungicides, or combinations thereof. The composition can be formulated to be coated on a plant, plant part, plant tissue (e.g., root or leaf), or seed. In certain aspects the F-ASO is combined with one or more excipients, buffering agents, carriers, etc. Such components are well known in the art and readily chosen for various applications by one skilled in the art.

Typically, a F-ASO of the present invention is provided to a target insect pest, target plant in need of treatment, or target microbe in an amount sufficient to inhibit production of the polypeptide encoded by one or more of the full-length genes targeted by F-ASOs. For example, when an insect pest is feeding on F-ASO-laden plant material (e.g., leaf), the insect ingests a sufficient level of F-ASO to result in a phenotypic effect on a bacterium harbored in its gut. In some embodiments, a combination of two or more F-ASOs can be combined in a single plant. In embodiments where two or more F-ASOs are combined in a single plant, the F-ASOs can target different genes or different portions of the same gene from the same or different targets. Thus, in one embodiment, a single plant material can be used to deliver multiple, different F-ASOs targeting the production of one or more proteins made by the treated plant, the insect pest, and/or a microbe present in the plant or in the insect. Where two or more F-ASOs are taken up and distributed throughout the plant material, the F-ASOs can be provided to the plant in a single solution, or in multiple, sequentially-applied solutions.

In addition to F-ASOs, compositions of the present invention that are intended to be applied to a plant can also comprise one or more chemoattractants, phagostimulants, visual attractants, insecticides, pheromones, fungicides, or combinations thereof. Such additional components are well known in the art and are readily chosen to complement compositions of the present invention, but are not specifically integral to the present invention. These additional components can be formulated to be coated on a plant, plant part, leaf, fruit, vegetable, stem or other plant structure. In certain aspects the additional component(s) are combined with one or more excipients, buffering agents, carriers, etc. that are also well known in the art.

Where additional components are applied in a coating, the coating can be formulated as a spray or dip so that the additional non-F-ASO components remain on the exterior of the plant material. For example, a leaf having a F-ASO distributed through at least part of its vascular system can be coated with a composition comprising one or more chemoattractants, phagostimulants, visual attractants, insecticides, pheromones, fungicides, or combinations thereof. Alternately, the additional component can be mixed with an aqueous solution containing the F-ASO(s) to be taken up and distributed via vascular action of the plant material, or osmosis through the plant material, thus distributing the F-ASO(s) and the additional component(s) throughout at least part of the plant material.

Application to Target Plants

Compositions of the invention disclosed herein can be applied to soil, fruits, vegetables, crops, and any other desired target using any delivery methodology known to those of skill in the art. For example, F-ASO-containing compositions can be applied to the desired locale via methods and forms including, but not limited to, shank injection, sprays, granules, flood/furrow methods, sprinklers, fumigation, root soaking and drip irrigation. In embodiments of the invention where the compositions are sprayed onto a desired locale, the compositions can be delivered as a liquid suspension, emulsion, microemulsion or powder. In other embodiments, granules or microcapsules can be used to deliver the compositions of the invention.

The compositions of the present invention can be applied to plants and/or crops by any convenient method, for example, by using a fixed application system such as a center pivot irrigation system. Preferably, application to fields of plants and/or crops is made by air spraying, i.e., from an airplane or helicopter, or by land spraying. For example, land spraying may be carried out by using a high flotation applicator equipped with a boom, by a back-pack sprayer or by nurse trucks or tanks. One of skill in the art will recognize that these application methodologies are provided by way of example and that any applicable methods known in the art or developed in the future can be utilized.

Having generally described this invention, the same will be better understood by reference to certain specific examples, which are included herein to further illustrate the invention and are not intended to limit the scope of the invention as defined by the claims.

EXAMPLES

Example 1

Production of F-ASO Molecules

All F-ASOs reported herein (SEQ ID NOs: 1-70 were produced utilizing an adjusted version of previously reported methods (Wilds & Dahma, Nucl. Acids Res., (2000) 28:3625-35). All of the F-ASOs reported herein were synthesized as 21-mers having, from 5'-3', six 2'-deoxy-2'-fluoroarabinonucleotides (2'F-ANA), nine 2'-deoxyribonucleotides, and six 2'-deoxy-2'-fluoroarabinonucleotides (Table 2, Formula 6).

Example 2

Delivery of F-ASO to Plant Tissues and to Feeding Insects Via Plant Tissues

Delivery of FASO to Plant Tissues (Cuttings)

Citrus cuttings were obtained and prepared as previously described (Andrade & Hunter (II), supra)). In brief, the new growth shoots from citrus trees (sweet orange, sour orange, grapefruit, and Carrizo, a rootstock variety), ornamentals (*Murraya paniculata*, periwinkle), and vegetables/herbs (okra, basil, sunflowers, grapevines) were cut and washed in 0.2% hypochlorate solution, 10 min, then twice with deionized water, 10 min, each time. The cuttings had all but the most apical leaves removed (3 leaves, or leaflets), and the stem or petiole end was cut while held underwater at approx. 45 degrees with a new, clean razor. The cutting was then placed into a vial, 1.5 mL or 2.0 mL which held a range of treatment solutions from 10 nMoles to 50 nMoles, (0.18 µg/µL to 1.5 µg/µL) of SC-ASO-1 (SEQ ID NO:1) in solution. The ASO solution was absorbed into the cuttings within 6-8 hrs, after which the vials were filled with Milli-Q filtered water and the tops wrapped with parafilm to reduce water loss. The samples were maintained as needed from 2 days to 40 days depending upon the bioassay.

Exemplary results are shown in FIG. 1. The leaf was visualized using confocal microscopy, scanning through the leaf at approx. 12-micron steps as advanced through the tissue analyses. The fluorophore-labeled 2'F-ANA oligonucleotide was detected in leaf palisade mesophyll, spongy mesophyll tissues and vascular bundles. demonstrating F-ASO distribution through leaf tissues and not limited to vascular tissues.

Delivery of F-ASO to Plant Tissues (Foliar Spray)

Figure 2:
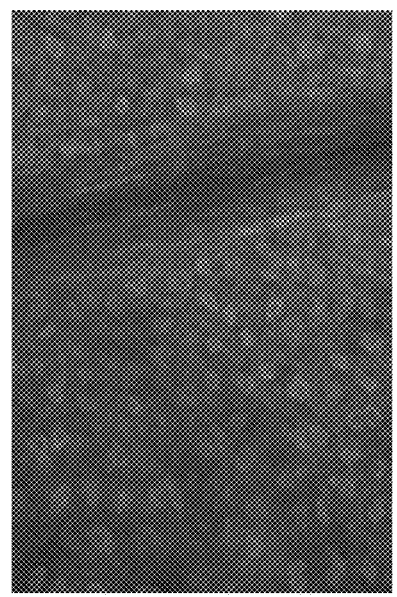
FIG. 2 provides an image of leaf tissue distribution of fluorescently labeled 2'F-ANA oligonucleotide (SC-ASO) through leaf tissues following application of the F-ASO as a foliar spray. Shown is a stacked light image with confocal deep scan through a sweet orange leaf.

Citrus cuttings, approximately 15 cm long, were sprayed with a water solution of a scrambled control ("SC-ASO-1"; SEQ ID NO:1) labeled with fluorophore. The citrus leaves were in a group of six which were sprayed and then left on the counter to dry (22-24° C. (room temperature)) prior to providing feeding access to citrus weevil, or psyllids (see below). A cohort of control leaves which were treated identically but without insects was collected and processed at 8 days post treatment. A leaf clearing solution was prepared by mixing equal parts of filtered Milli-Q water, glycerine, and 4 M acetic acid. Then 10M NaOH was added bring the pH between 5.0 to 5.8. Two cuttings from each group were placed in the clearing solution. One cutting from each group, was placed into a 1 L beaker with 100 mL of clearing solution. These were autoclaved set on the liquid cycle (L3), 1 hour, with a heating time of 30 minutes at 121° C. at peak cycle run. The leaves or cut leaf pieces were then gently washed and mounted onto glass slides using an anti-quenching solution (Fluoromount™) and a phosphate buffered solution, PBS, pH 7.0, in water. The prepared leaves were examined with a confocal microscope at the specific fluorophore emission/excitation. Controls were examined first and set so that no fluorescence was observed. The same microscope settings were not altered but were then used to view treated samples from the same experiment to determine the visibility of labelled SC-ASO probe. Results are shown in FIG. 2, showing uptake by plant tissues of F-ASO after foliar spray application.

Insect Feeding Assays

Psyllid feeding assay (plant cuttings): Citrus psyllid adults were provided feeding access on new citrus growth cuttings post absorption (cuttings were treated with a solution of 10 nmoles SC-ASO-2 (SEQ ID NO:2) or water). To validate F-ASO delivery into the adult psyllid tissues, the labeled cohort were sacrificed five or nine days post feeding access and processed for confocal analyses for presence of the F-ASO. The mortality was recorded for the F-ASO treated and average mortality was compared to both the water blank control, and the unlabeled F-ASO.

Weevil feeding assay (plant cuttings): Weevil adults were provided foliage which had topically applied sprays of SC-ASO-1 (SEQ ID NO:1) onto citrus cuttings approximately 12 to 20 cm long. Then 20 adults (10 male/10 female) were caged with a bouquet of treated sweet orange cuttings, and provided two sets of wax paper strips for the females to oviposite egg masses. Controls used the scrambled SC-F-ASO, and a water-only blank control on citrus cuttings.

Weevil feeding bioassay (artificial diet): Weevil larvae or adults, either male or female, were provided SC-ASO-1 (SEQ ID NO:1) mixed into commercial diet (Lapointe et al, J. Insect Physiol. (2008) 54:1157-67) for larvae, or a 10% to 30% sucrose water solution for adults.

In preparation for visualization using confocal microscopy, the psyllid tissues were fixed in 4% paraformaldehyde and dehydrated through a series of graded ethanol (35%, 50%, 70%, 80% 90%, 100% three changes) 30 min each step, overnight in 70% or greater concentration as needed. The samples were then mounted in Fluoromount™ on glass slides and viewed within 24 to 48 hrs. Samples were kept covered and in the dark prior to being examined. Weevils were prepared similarly but organs and tissues were dissected from their bodies, fixed and then mounted on glass slides for visual analyses by confocal microscopy.

Figure 3:
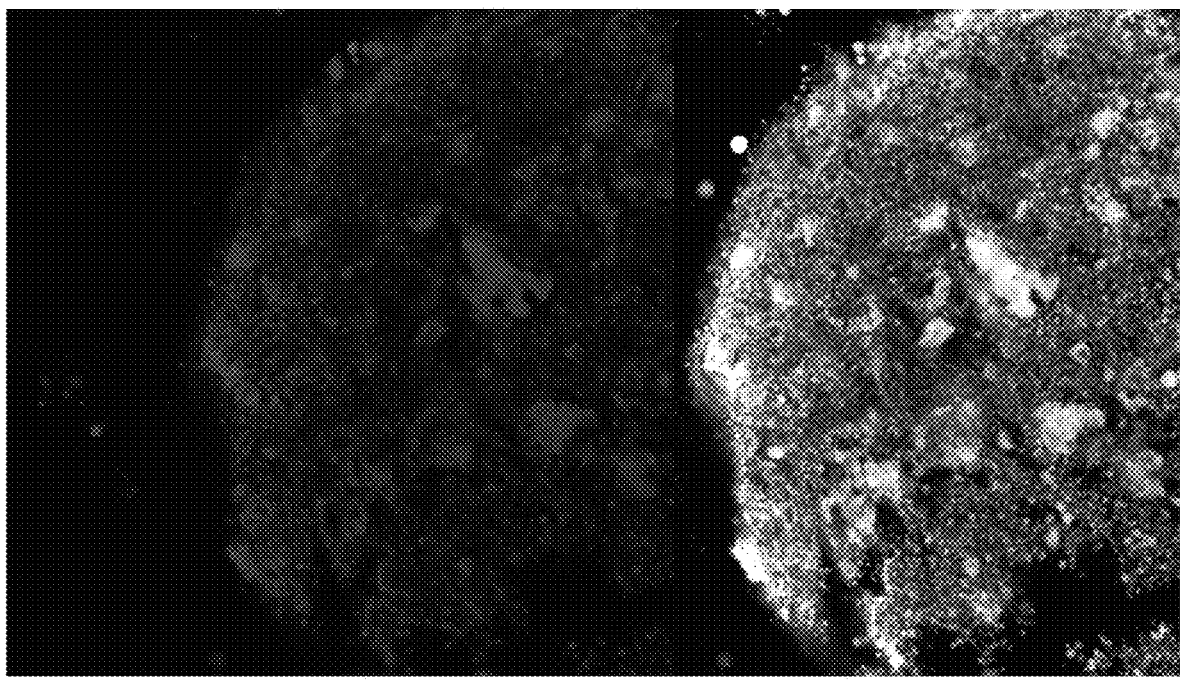
FIG. 3 provides an image showing the detection, using confocal microscopy, of labeled F'-ANA oligonucleotide (SC-ASO) in *D. abbreviatus* eight days post ingestion. The F-ASO are present in the insect's supra-esophageal ganglion (brain), post feeding on citrus cuttings which were treated with foliar topical sprays.
Figure 4:
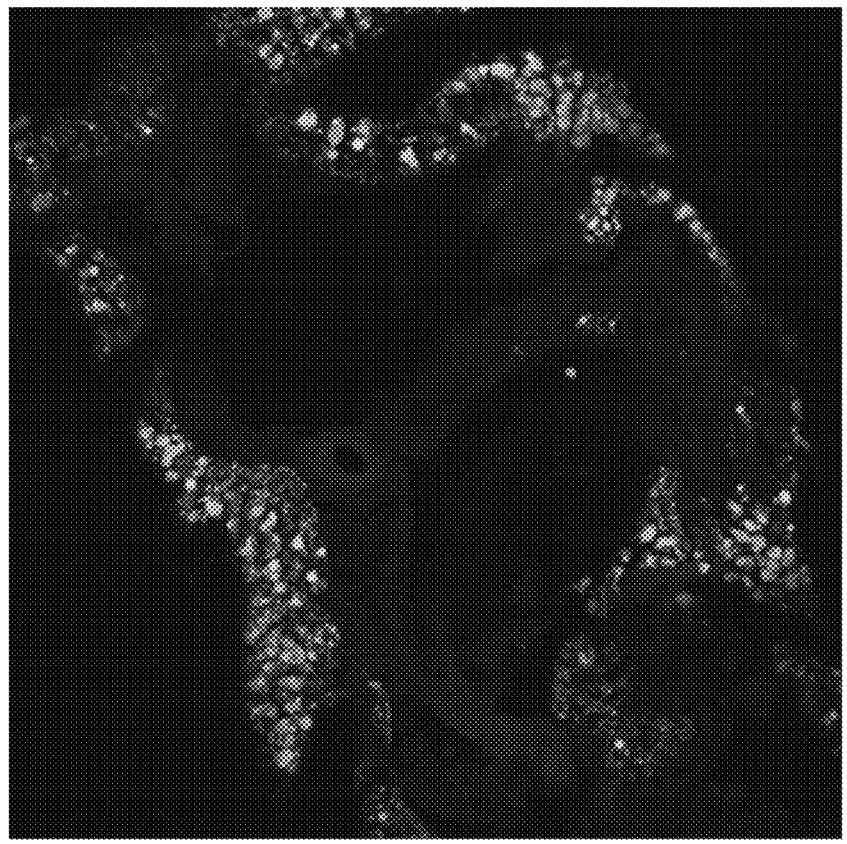
FIG. 4 provides an image showing the detection, using confocal microscopy, of labeled F'-ANA oligonucleotide (SC-ASO) in *D. citri* five days post-ingestion from treated cuttings.
Figure 5:
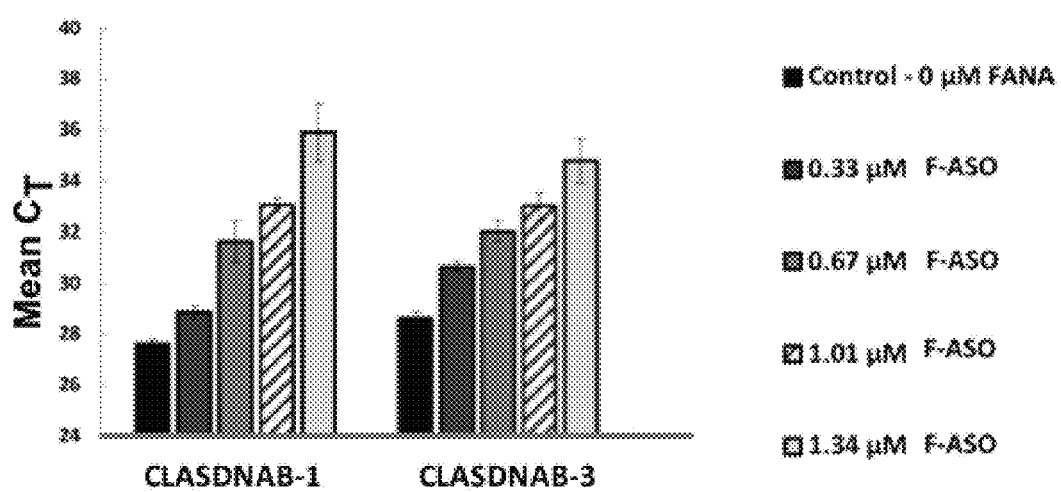
FIG. 5 provides a representation of data showing the effect of various concentrations of F-ASOs targeting a *D. citri* transcript in an in vitro binding assay.
Figure 6:
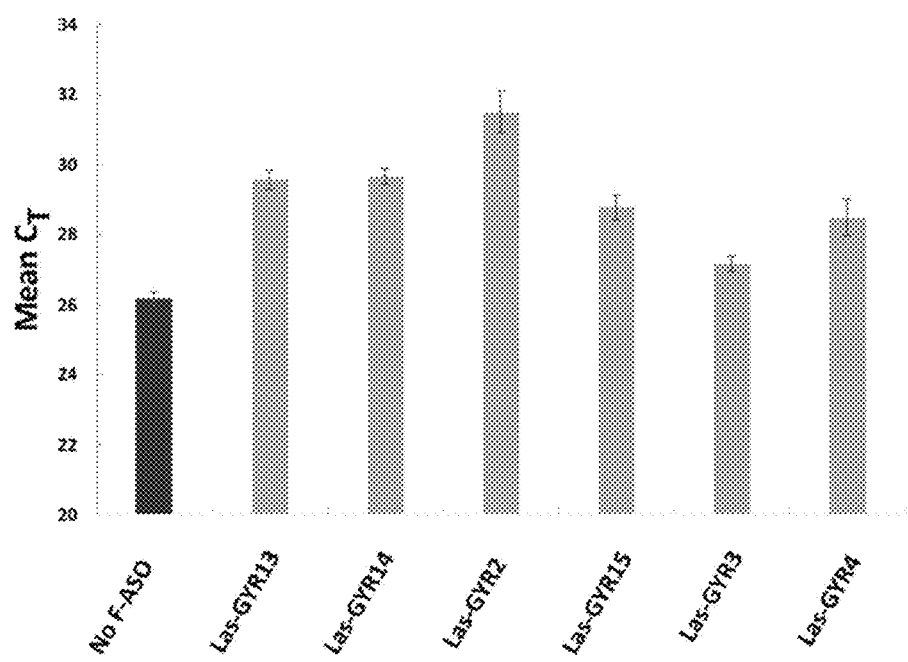
FIG. 6 provides a representation of data showing the ability of F-ASOs targeting a CLas transcript to bind to their target isolated from infected psyllids in an in vitro binding assay.

Analyzed samples from weevils (*D. abbreviatus*; FIG. 3), which are leaf chewing insects, and citrus psyllids (*D. citri*; FIG. 4), which are phloem feeding insects, demonstrated that feeding on F-ASO treated cuttings and plant tissues led to ingestion and distribution of the F-ASO into various tissues.

Delivery of F-ASOs Via Soil Treatment

Insects were also provided feeding access on citrus and other plants which were treated with F-ASOs via soil treatment. F-ASO were applied to potted plants either in water (SC-ASO-1—SEQ ID NO:1), or absorbed into clay pellets which were then mixed into the potting soil (SC-ASO-1—SEQ ID NO:1; or test F-ASOs). Both routes of soil treatment showed sufficient delivery for ingestion by insects with subsequent watering for root absorption and systemic movement of the F-ASOs throughout the plant tissues.

An F-ASO (SC-ASO-1; SEQ ID NO:1) solution was prepared by mixing 200 nmoles (1.6 mg) of the oligonucleotide in 100 mL water for plants potted in pots or containers 1 gal or larger in volume. The soil was not watered for two days, and then the treatment was applied. Within 1 hour of treating the soil, an additional application of water alone, 100 mL, no product, was applied to ensure the soil in the pot was adequately wetted. Plastic drip pans below the pots caught any runoff, which was poured back into the soil 2 hours post treatment. Clay absorbent treatment in soil used the same concentration—200 nmoles (1.6 mg) of F-ASO (SC-ASO-2; SEQ ID NO:2) mixed in 25 mL water. This solution was poured into a 50 mL centrifuge tube holding 35 grams of granular dry clay particles. The cap was screwed onto the tube and shaken to mix the clay absorbent and F-ASO solution. The 35 grams of wet absorbent was added into half the volume of potting soil to fill the top half of the pot when repotting plants. At one hour post potting, 100 mL of water alone (no product) was poured onto the soil again to provide adequate water for root absorption. Plants were then watered on a schedule of 100 mL water every three days for the duration of the experiment. Any run through of water was collected in drip trays beneath the pots and poured back into the soil. Insects were provided feeding access to these potted plants. Confocal microscopy of plant and insect tissues revealed similar results to those shown for insects feeding on treated cuttings, or topically applied foliar sprays.

Insect Feeding Assay (Artificial Diet)

For feeding assays, delivery of F-ASO was achieved utilizing sucrose solutions (10-30%) in water for plant feeding hemipterans (psyllids), or in diet mixtures suitable for mass rearing and culturing of beetle larvae, or lepidopteran larvae (Lapointe et al, J. Insect Physiol., (2008) 54:1157-67: Silva & Parra, Rev. Bras. Entomol., (2013) 57:347-9). The diet for chewing insect larvae (weevils) was treated with 7 nmol to 10 nmol (63 µg to 90 µg)SC-ASO-1 (SEQ ID NO:1) which was labeled with a fluorophore probe. Larvae were provided feeding access (24 hours) to either a diet treated with fluorescently labeled SC-ASO-2 (SEQ ID NO:2) (red) or untreated diet. At 9 days post feeding, Larval midgut tissues were dissected, fixed and mounted for observation using confocal microscopy. Larvae were processed and examined on the same day they were collected. The F-ASO probe was visualized in a wide range of insect tissues, similar to the results from feeding trials in weevils and psyllids.

Delivery of FASO to Plant Tissues (Multiwell Plates)

A 48-well leaf disc assay can be used to screen for efficacy of F-ASO to reduce CLas in leaves of infected citrus trees (Valencia sweet orange (*Citrus sinensis* (L.) Osbeck). Valencia orange plants, previously validated to be CLas infected, were used as infection source material. Extracted nucleic acids were used for quantitative real-time PCR (qPCR) using primers and probe according to standard protocols. The method reduces variation and increases normalization of CLas copy number across citrus leaves from one tree. A set of 4 to 12 leaves per tree were collected and processed individually. The petiole or proximal end of the leaf which would be attached to the tree is cut and collected (8.0 to 8.5 mm in length) to be used as a pretest to validate CLas positive leaves (qPCR methods and primers, positive if Ct value less than 36). Five to six discs were punched along the midrib of CLas positive leaves starting from the proximal end. The leaf discs were floated on solutions containing individual F-ASOs targeting CLas DNA Ligase B (SEQ ID NO:4, SEQ ID NO:5, SEQ ID NO:6, and SEQ ID NO:7), at approximately 50 nM to 100 nM concentration in basal salt mixture, M524 (PhytoTechnology Laboratories, Shawnee Missions, KS, 66282, USA). The individual leaf discs were collected and analyzed at 1 hr and 24 hr post treatment. The extracted samples were run as technical replicate reactions in qPCR analyses. The Total CLas genome equivalents, gDNA, were compared to the CLas RNA Ct value to calculate CLas equivalents (Cangelosi & Meschke, Appl. Environ. Microbiol., (2014) 80:5884-91). A bacterial RNA/DNA ratio was calculated to get the indicator for live bacteria.

An in vivo assay was performed by collecting CLas infected leaves and validating infection (CLas copy number) by screening the petioles using real-time PCR, as previously described. Five leaf discs (10 mm diameter) were punched out with metal cork bore tool, down the midrib of each leaf and placed in a 48-well plate that contained 100 µL sterile water. The first two leaf discs closest the petiole were treated with individual F-ASOs targeting CLas DnaB helicase (SEQ ID NO:4, SEQ ID NO:5, SEQ ID NO:6, and SEQ ID NO:7). The leaf disc samples were collected at 1 hr and 24 hr, then homogenized under liquid nitrogen, and stored in Trizol reagent. Total RNA isolation was performed using Zymo Research Direct-Zol RNA Microprep kit. Analysis using qRT-PCR was performed using primers to CLas previously reported in the literature (Li et al, J. Microbiol. Meth., (2006) 66:104-15), primers to the CLas replicative DnaB helicase gene, and primers to the citrus dehydrin gene as the internal leaf control. The qPCR analysis showed that for leaf disks treated with F-ASO there was a significant reduction in CLas titer 24 hr post treatment; (about a 10-fold decrease) indicated by the $C_T$ change from 30.34 at 1 hr; to 33.19 at 24 hr. (a 2.85 $C_T$ change differential). The scrambled control, SC-ASO treatment and the leaf internal control dehydrin only varied by 1.08 and 0.84 $C_T$ respectively.

The change in $C_T$ mean values at 24 hr post treatment were determined. CLasDNAB-1 (SEQ ID NO:4), treated citrus leaf discs which were infected with CLas showed significant decrease in titer with an increase of 2.85 $C_T$ from stating concentrations. The qPCR analysis showed that for leaf disks treated with F-ASO there was a significant reduction in CLas titer 24 hr post treatment—about a 10-fold decrease indicated by the $C_T$ change from 30.34 at 1 hr; to 33.19 at 24 hr. (a 2.85 $C_T$ change differential). The unlabeled scrambled control treatment (SC-ASO-3; SEQ ID NO:3) and the leaf internal control (dehydrin) only varied by 1.08 and 0.84 $C_T$ respectively.

Example 3

F-ASO Binding Affinity Bioassay (In Vitro)

Individual F-ASO molecules were evaluated for binding affinity in vitro using either nucleic acid extractions from psyllids reared on CLas-infected citrus, or reared on non-infected citrus of the same plant variety (Madam vinous). The psyllid stock sample was prepared using 50 adult psyllids which had been reared from eggs on CLas-infected citrus seedlings in culture (Insectary, USDA, ARS, Fort Pierce, Fla.). Total RNA was extracted using a RNA kit (Qiagen) then amplified, gel purified, and used as a template to produce mRNA transcript (bacterial transcripts in this example, psyllid transcripts produced similarly).

Analysis using qPCR determined concentration $C_T$ values (delta-delta $C_T$, software) detecting bacterial transcripts from extracts from CLas-infected citrus plants, or from CLas-infected psyllids reared on infected citrus plants. Non-exposed citrus or psyllids were used as controls. Individual F-ASOs targeting CLas DnaB helicase (SEQ ID NO:4, SEQ ID NO:5, SEQ ID NO:6, and SEQ ID NO:7) were spiked into the purified transcripts of CLas solution prepared from infected adult psyllids. Analyses across a concentration gradient demonstrated a dose dependent suppression of CLas with the F-ASOs. Concentration gradient (0.0 µM (control), Treatments at: 0.33 µMoles, 0.67 µM, 1.01 µM, 1.34 µM). The analyses showed a positive correlation between increasing $C_T$ values (representing reduced bacteria), with increasing concentrations of F-ASO added into the samples (FIG. 5 shows exemplary results using SEQ ID NO:4, and SEQ ID NO:6).

PCR Validation of the Bacterial Transcripts in CLas

DNA isolated from CLas bacterium from infected citrus trees was used to validate primers needed for each experiment. Positive control primers amplified RNA polymerase sigma 70 factor and 16S region from the bacteria. Each reaction consisted of 1 μL DNA, 0.5 μL of 10 μM of each target-specific primer, and 23 μL Platinum® PCR SuperMix (Invitrogen). PCR was performed in an MJ Research Peltier Thermal-cycler using the following parameters: 3 min at 92° C., followed by 45 cycles of 30s at 92° C., 30s at 60°, and 60s at 72° C., and a single final cycle of 72° C. for 10 min. All PCR reactions were performed in technical replicates. 10 μL of each replicate was fractionated by electrophoresis for 45 min in a 2% agarose gel stained with ethidium bromide.

Binding of FASO to Transcript mRNA Regions In Vitro Prescreening

Five aliquots consisting of 5 ng purified target transcript were prepared in 0.2 mL microcentrifuge tubes. Each aliquot was treated with a single F-ASO and nuclease free water to dilute samples to final concentrations of: 0 μM (control), 0.34 μM ASO, 0.67 μM ASO, 1.01 μM ASO, and 1.36 μM ASO. Samples were vortexed gently and incubated at room temperature for 30 min. Relative binding of each single ASO to each transcript target was quantified using qPCR.

PCR Validation of F-ASO Binding to CLas Gyrase a Transcript

Total RNA was isolated from CLas-infected psyllids using the Direct-Zol Microprep Kit protocol. Control: 100 ng of RNA was incubated with 3' gyrA reverse primer (200 nM). Treatments: in individual PCR reaction tubes, 100 ng of RNA was incubated with 3' gyrase-A reverse primer (200 nM) and spiked with F-ASOs (200 nM or 0.2 nanomoles) targeting the gyrA gene: Las-GYR2 (SEQ ID NO:8), Las-GYR3 (SEQ ID NO:9), Las-GYR4 (SEQ ID NO:10), Las-GYR13 (SEQ ID NO:19), Las-GYR14(SEQ ID NO:20), and Las-GYR15 (SEQ ID NO:21).

qPCR Profile, Reverse Transcriptase Real Time PCR

Efficacy of target binding was analyzed by quantitative rtPCR. In brief, each sample was analyzed in three replicate reactions that consisted of: 2 μL sample, 0.5 μL of 10 methods previously described. Reference dye used at 1 μL ROX (diluted 1:10), 12.5 μL PLATINUM SYBR Green qPCR SuperMix-UDG, and 8.5 μL of nuclease free water. Quantitative PCR was performed in an Applied Biosystems 7500 Real-Time PCR System with the following parameters: 2 min at 50° C., 10 min at 95° C., followed by 40 cycles of 15 s at 95° C. and 30 s at 60° C. Melting curve analysis was also obtained following completion of the final cycle. Binding efficiency was correlated with software predictions for each F-ASO molecule and the Mfold prediction for the mRNA.

Results

The F-ASO Las-GYR2 (SEQ ID NO:8) resulted in the greatest binding to target and increased the $C_T$ value by approximately 5.2 units, followed by Las-GYR13 (SEQ ID NO:19) and Las-GYR14 (SEQ ID NO:20) which increased the $C_T$ values by 3.5 units, then LasGYR15 (SEQ ID NO:21) and Las-GYR4 (SEQ ID NO:10) which increased $C_T$ values by 2.4, and finally Las-GYR-3 (SEQ ID NO:9) which increased the $C_T$ by 1. Values show there is variability upon each testing of each individual F-ASO for affinity to CLas_GyrA (FIG. 6, error bars represent standard deviation of three technical replicates). This demonstrated that not every F-ASO has the same efficacy even though they can be designed to bind to the same transcript. The location on the mRNA and the predicted folding identified potential secondary structures and locations which would not be suitable for efficient F-ASO target binding on the mRNA. Evidence of binding sites, which would include hairpin-like complementary structures, as well as mistakes in design of the F-ASO that might include complementary ends could result in folding and binding of the F-ASO shut. This could produce a nonfunctional hairpin and, should therefore be evaluated and avoided prior to designing antisense oligos.

Example 4

Treatment of CLas Infection by Tree Trunk Injection

A citrus seedling trial was conducted which mixed equal aliquots of F-ASOs targeting the CLas DNA Ligase A transcript: CLIBASIA-1 (SEQ ID NO:22), CLIBASIA-2

(SEQ ID NO:23), CLIBASIA-3 (SEQ ID NO:24), CLIBASIA-4 (SEQ ID NO:25), and CLIBASIA-5 (SEQ ID NO:26) mixed together at equal 100 µM each in water to a final concentration of 500 µM. A scrambled control F-ASO without probe, was used at 100 µM. Each treatment was injected into the trunks of two sweet orange (Madam vinous) seedlings. Trees were previously validated to be CLas-infected using qPCR analysis. Weekly samples were collected and processed for qPCR analyses, and a second analysis of live/dead bacteria (PMA-qPCR, live/dead assay, as described above). Each sample collection included 4 leaves which were showing symptoms per tree. At three weeks post treatment a reduction of CLas genome equivalents was measured.

The infected citrus seedlings were contained in a glasshouse, at the USDA research lab (U.S. Hort. Res. Lab., Fort Pierce, Fla.) growing in 3.78 L (1 gal) black plastic octagonal DeepPots™. The trees were 1.5 to 2.0 M tall, with no fruit. Two trees were used for each treatment. 1) Control (water only); 2) No probe control SC-ASO-3 scrambled (SEQ ID NO:3); and 3) the F-ASO mixture (CLIBASIA-1 (SEQ ID NO:22), CLIBASIA-2 (SEQ ID NO:23), CLIBASIA-3 (SEQ ID NO:24), CLIBASIA-4 (SEQ ID NO:25), and CLIBASIA-5 (SEQ ID NO:26)).

Bacterial Infection Decreases (CLas gDNA Titer)

Figure 7:
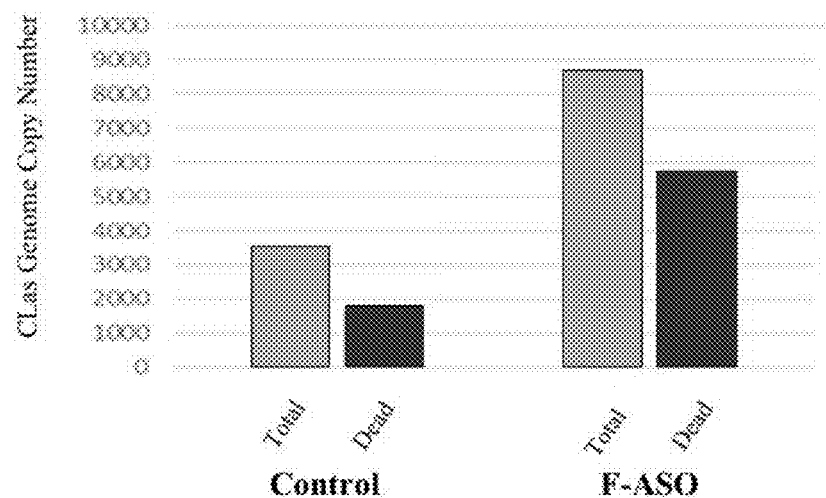
FIG. 7 provides a representation of data showing total and dead CLas genome copy number 30 days post-F-ASO treatment using tree trunk injection.
Figure 8:
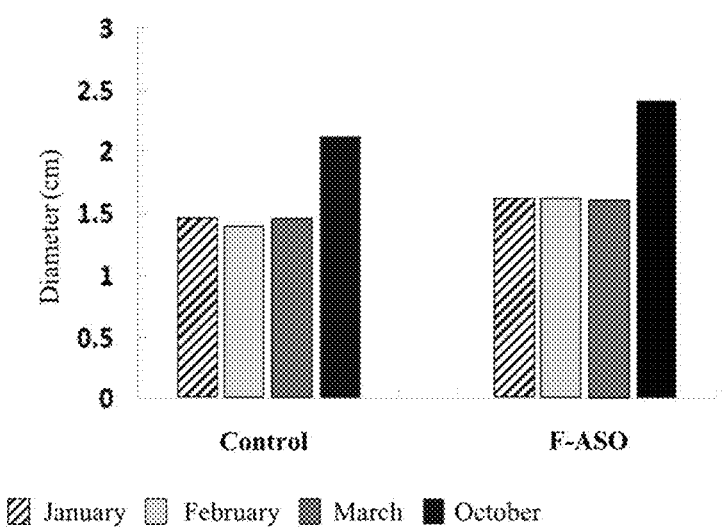
FIG. 8 provides a representation of data showing changes in tree trunk circumference between control (untreated) CLas-infected trees and trees receiving an anti-CLas F-ASO.
Figure 9:
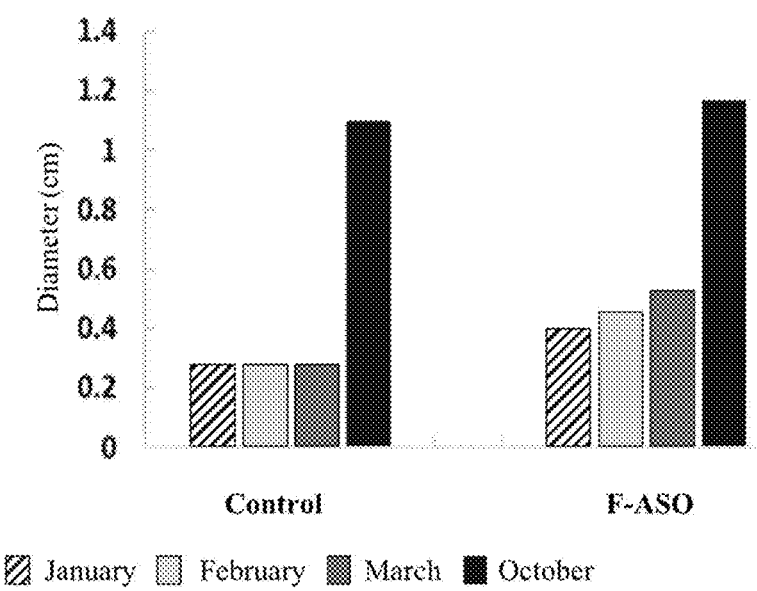
Figure 10:
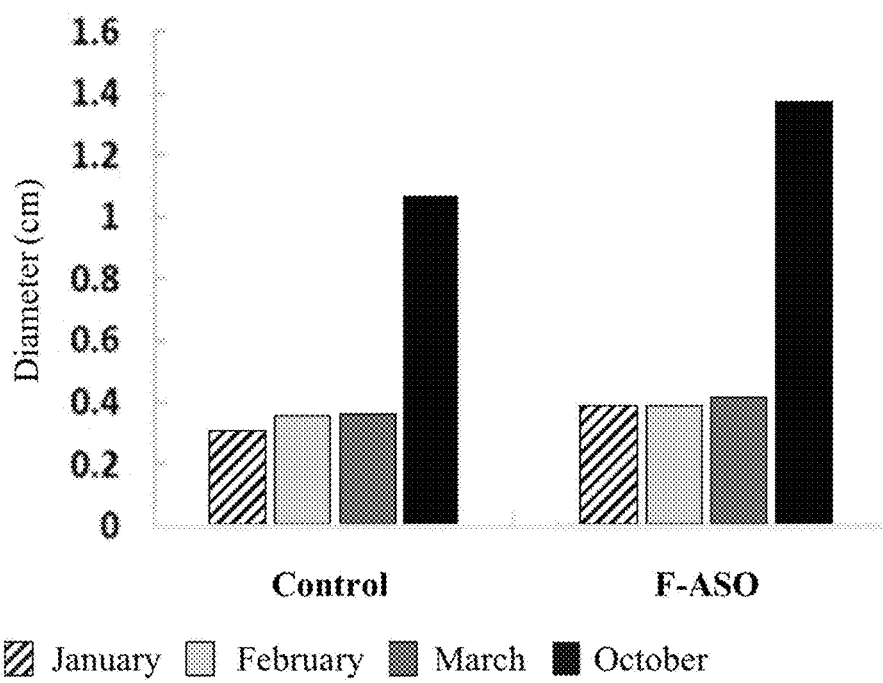

The total DNA titer, which includes dead and live bacterial gDNA, was calculated in genome equivalents using the PMA-qPCR method, allowing for distinguishing live genomes and dead genomes. Results are shown in FIG. 7 where total versus dead bacterial copy number shown as a percentage of the total copy. The difference from control is used as indicator of increased mortality due to treatment. (Two plants per treatment in this trial). Analysis was done at 30 days post treatments. F-ASO treated trees had more dead CLas bacteria, (65.5% CLas mortality), which was 17.3% greater than the untreated CLas infected control trees (48.2% CLas mortality).

Tree Growth (Trunk and Branch Diameter)

In most glasshouse research trials, the CLas is inoculated into citrus by grafting. To better mimic the natural process of CLas transmission by citrus psyllids, citrus seedlings were inoculated using CLas reared psyllid adults. The CLas-infected citron (*Citrus medica*) served as the source of inoculum. Cages held free-ranging psyllids to vector the pathogen, to a trial of 16 citrus genotypes (*C. medica, C. reticulata, C. grandis, C. sinensis, C. x paradisi, Poncirus trifoliata*, and nine citrus hybrids) as hosts. The experiment was conducted three times. Leaf samples were collected at regular intervals over a period of approximately 300 days and each sample was assayed for the presence of CLas, by qPCR methods. In each experiment, CLas titer remained at less than $10^1$ copies 16S rDNA genomes until 150 to 175 days after placing CLas negative trees into the glasshouse. CLas titers increased steadily for the remainder of the experiments. After 300 to 350 days in the glasshouse the final means for CLas titer ranged from $10^3$ to $10^5$ $g^{-1}$ fresh weight, although HLB symptoms were not apparent. Significant differences in CLas titer among the cultivars were first detected at approximately 125 days post exposure.

Figure 11:
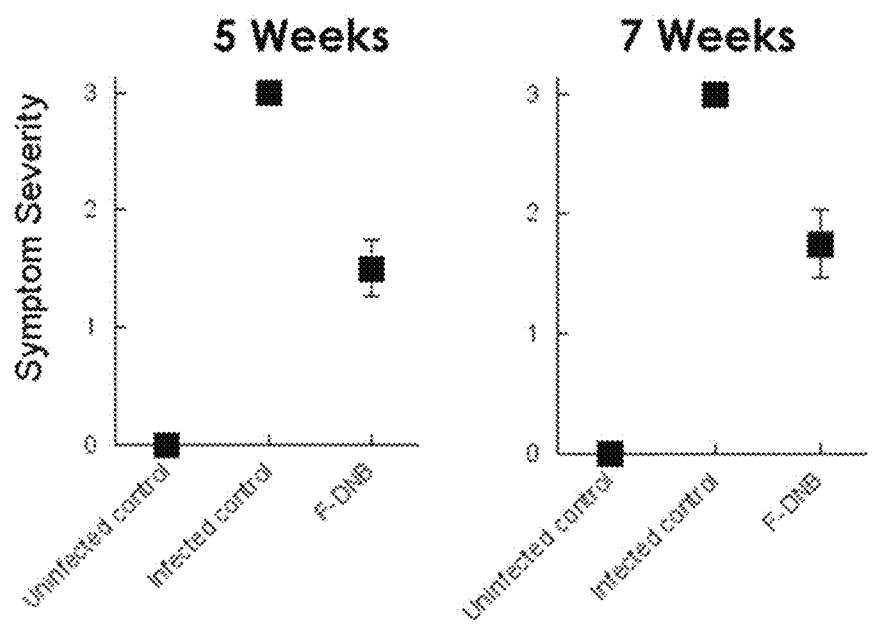

As changes in plant traits are standard indicators of citrus tree health, tree trunk circumference and branch diameter were recorded using a measuring tape and digital calipers. Values were recorded in cm. Measurement of the tree trunk was take at the top of the pot edge, and two branches per tree had marked locations for repeated measurements of branch diameters. Calipers were used to measure the maximum diameters at marked locations on each citrus tree over 12-month period post treatment with the mixture of F-ASOs targeting CLas DNA Ligase A transcript (CLIBASIA-1 (SEQ ID NO:22), CLIBASIA-2 (SEQ ID NO:23), CLIBASIA-3 (SEQ ID NO:24), CLIBASIA-4 (SEQ ID NO:25), and CLIBASIA-5 (SEQ ID NO:26)). Each treatment had 5 sweet orange, citrus seedlings 2 years of age, grown in 1 gal pots in a glasshouse with constant 16/8 L:D photoperiod. All trees were grown under the same water and fertilizer program with plants randomized on the glasshouse bench. Measurement of the main tree trunk over the 12-month period, resulted in an increase of 2.4 cm in the F-ASO treated trees, compared to 2.1 cm increase in the control (FIG. 8). Measurement of the two branches (A & B) per tree over the 12-month period resulted in an increase of 1.2 cm in the F-ASO treated trees, compared to 1.1 cm increase in the control for branch-A (FIG. 9). The average change in diameter for branch –B, resulted in an increase of 1.4 cm in the F-ASO treated trees, compared to 1.1 cm increase the control (FIG. 10).

Example 5

Targeting CLso in Infected Potato and Potato Psyllid

Potatoes and citrus are both under threat from a bacterial species *Liberibacter solanacearum*, (CLso), which is related to CLas and also has a psyllid vector species. Therefore, we tested our system in potato plants against CLso. Potato "Ranger Russet" plants were grown under greenhouse conditions from certified virus-free tubers in 15 cm pots filled with MIRACLE GROW® potting mix. Plants with at least four leaves were used in experiments (about 10 days old). Separate colonies of *Liberibacter*-infected and uninfected *Bactericera cockerelli* (potato psyllid) were maintained on potato at 25° C. with a 16:8 (L:D) hrs. photoperiod. The Northwestern haplotype of *B. cockerelli* and "*Candidatus Liberibacter solanacearum*" CLso, haplotype B were used in the experiments. Plants were infested with infected or non-infected psyllids 1-week prior to treatment applications by confining ten psyllids to the terminals of each plant using a sleeve cage. Treatments included 1) uninfected water control, 2) infected water control, 3) infected treated with CLso-DNAB-3 (SEQ ID NO:28).

CLso DNAB Target

The F-ASO targeting the DnaB gene in CLso-infected potato (CLsoDNAB-3 (SEQ ID NO:28)) is similar to a F-ASO described above targeting the CLas DnaB gene (CLASDNAB-3 (SEQ ID NO:6) from the CLas pathogen but with a single SNP difference. The CLsoDNAB-3 F-ASO (SEQ ID NO:28) was applied individually as a soil drench treatment to potted potato plants at a concentration of 100 μmoles of F-ASO in 100 mL water. Potted plants, five per treatment, were not watered for 4 days prior to being treated. Symptom analyses of CLso infected potato plants, post F-ASO treatments, resulted in delayed symptom expression. Symptoms from CLso infection normally show rapid yellowing of leaves 7-10 days post infection, however treated plants showed little to no symptoms compared to infected control plants at five weeks post treatment. Symptoms were scored 0 (none), to 3 (severe) (Sengoda et al, J. Econ. Entomol., (2013) 106:1964-72; Torres et al, PLoS ONE, (2015) 10:e0142734). None of the uninfected plants treated with water developed symptoms associated with infection by CLso, whereas all infected plants treated with water exhibited severe foliar symptoms at 5 weeks post initial inoculation. Infected plants treated with CLso-DNB-3 exhibited reduced symptoms that were intermediate to uninfected and infected controls and differed significantly on both dates from controls of uninfected and infected plants (approximately five weeks: F=22.2; d.f.=3, 9; P<0.001, Seven weeks: F=13.5; d.f.=3, 9; P=0.001) (FIG. 11).

CLso Gyrase-A Target

F-ASOs tested were a scrambled control (SC-ASO-3 (SEQ ID NO:3)) and CLsoGYR-2 (SEQ ID NO:30), CLsoGYR-3 (SEQ ID NO:31), CLsoGYR-4 (SEQ ID NO:32), and CLsoGYR-5 (SEQ ID NO:33). Plants (five per treatment) were inoculated with the zebra chip pathogen (CLso, haplotype 'B') by confining three *Liberibacter*-infected psyllids to a single leaf for one week. Control healthy plants were not challenged with psyllids. Following a 1-week inoculation access period, the psyllids were removed and CLso titers were analyzed using standard bioassay methods for DNA extraction, PCR amplification and real time PCR according to methods outlined in Liefting et al. (Plant Dis., (2009) 93:208-14) and Crosslin et al. (Southwest. Entomol., (2011)36:125-35), which are routinely used in the laboratory (Cooper et al, Environ. Entomol., (2017) 46:393-402). Three leaflets from three separate leaves were collected from each plant to quantify titers of the zebra chip pathogen using quantitative PCR as previously described. Each plant was then treated with 100 mM F-ASO solution (one of five target sequences or non-target control) or water (untreated controls) using a 100 ml soil drench. Development of foliar symptoms was monitored and photo-documented every 2 weeks and was ranked from 0 (no symptoms) to 3 (severe). Two weeks following the initial treatment, treatments were reapplied and three leaflets from separate leaves were collected from each plant to quantify pathogen titers.

Figure 12:
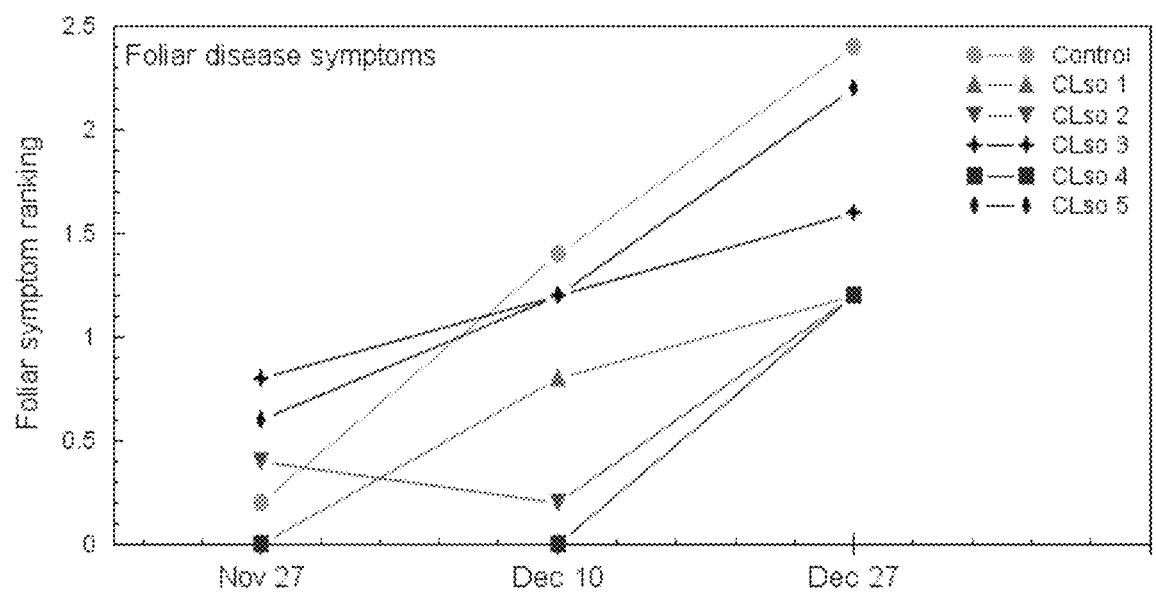
Figure 13:
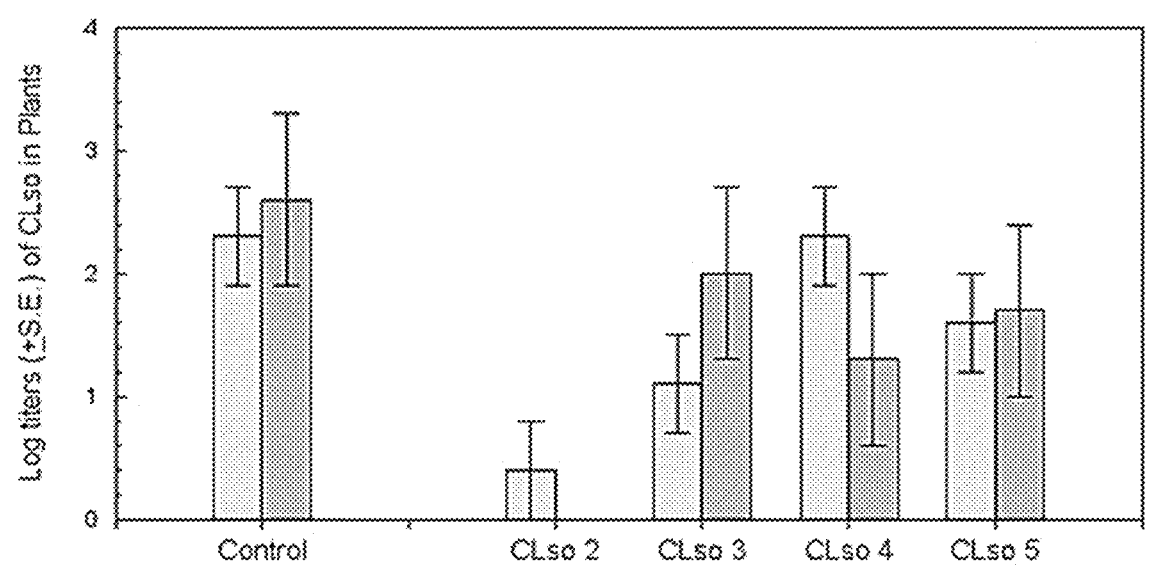

Infected plants exhibited reduced growth and flowering compared to uninfected plants, regardless of treatment. Foliar symptoms were delayed, but not eliminated, in plants treated with CLsoGYR-2 (SEQ ID NO:30), and CLsoGYR-4 (SEQ ID NO:32) (FIG. 12). CLso was not detected in uninfected plants on any sample date and was not detected in infected plants prior to treatments. In general, CLso titers were numerically reduced in treated plants compared with infected control two weeks after treatment. Previously CLso-positive plants resulted in negatives with no detection of the bacteria in plants treated with CLsoGYR-2 (SEQ ID NO:30) at four weeks post initial treatment, and were reduced in plants treated with CLsoGYR-4 (SEQ ID NO:32) (infected control 2.4 Ct and CLsoGYR-4 averaged 1.2) (FIG. 13).

Plants were in poor health when psyllids were removed to measure acquisition of the pathogen. Few living psyllids were collected from plants exhibiting severe symptoms. CLso was detected in psyllids removed from 2 of 5 plants treated with CLsoGYR-2 (SEQ ID NO:30). *Liberibacter* was not detected in psyllids removed from the remaining treatments (data not shown).

Figure 14:
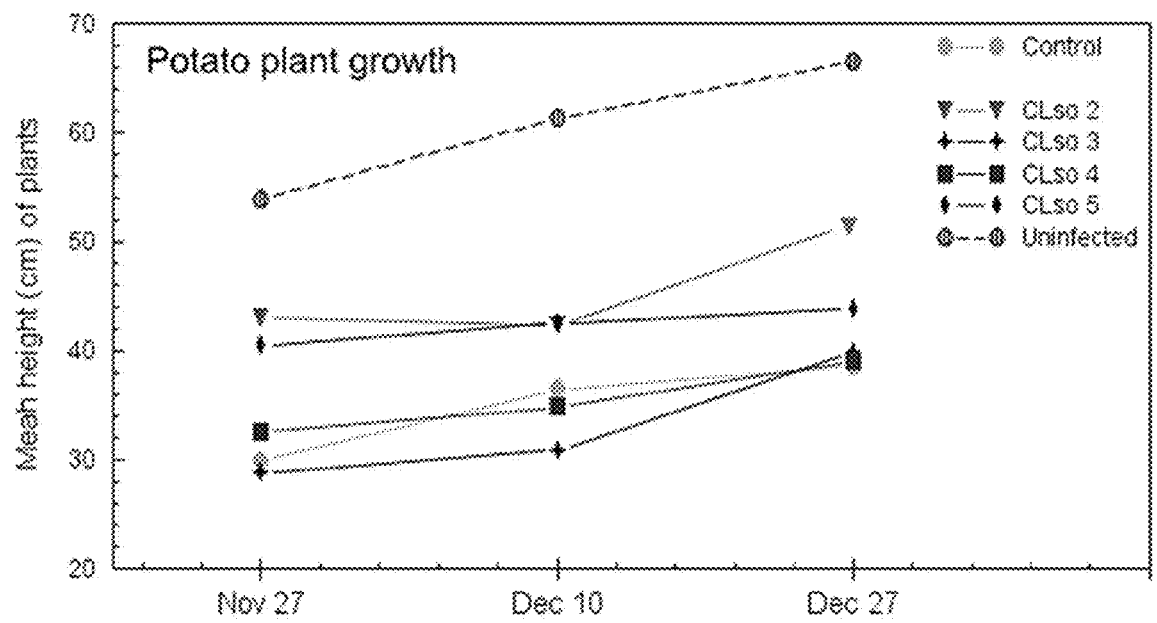

In general, plants treated with CLsoGYR-2 (SEQ ID NO:30), and CLsoGYR-4 (SEQ ID NO:32) exhibited delayed symptom development and reduced pathogen titer compared with CLso infected controls at both 2 and 4 weeks and had the greatest number of plants to become CLso-negative at 4 weeks (100% and 80%, respectively; FIG. 13). Improved plant growth (as indicated by height) resulted for treatments with CLsoGYR-2 (SEQ ID NO:30), and CLsoGYR-4 (SEQ ID NO:32) compared to infected controls (FIG. 14).

Example 6

Targeting Bacteria Inside the Asian Citrus Psyllid with F-ASO

To determine whether endosymbiotic bacteria could be targeted with F-ASOs, we delivered these products to *D. citri* primarily using treated citrus leaf discs in an artificial feeding chamber, a multiwall plastic plate. In some trials a diet (30% sucrose in water) was used.

For the feeding bioassay, a 300 µL volume of each F-ASO molecule was added to a 30% sucrose solution. The concentration of F-ASOs for feeding assays was calculated between 5 to 10 µM, on average, for liquid diets, and between 1 to 5 µM when treating plant cuttings or floating leaf disks. The standard controls were water (no F-ASO), and a scrambled control F-ASO (AUM-C1-SC-1; SEQ ID NO:46) without probe. Three replicates were performed for each treatment group. For psyllids, 16 adult psyllids which were CLas-infected (8 males and 8 females) were given a six-day feeding access period to treatments solutions, at 27° C. Samples were collected at 1 day and 6 days post feeding. Psyllids were sacrificed and the total DNA extracted using the QIAGEN DNeasy® Blood and Tissue Kit. Each sample was normalized to 50 ng/µL (NanoDrop™ 8000). Samples were run in triplicate on qPCR using 16S primers for each respective endosymbiont. The psyllid internal control was the *D. citri* mRNA for wingless. Standard rtPCR and qPCR methods were used as previously described.

CLas Ligase-A Targeted in CLas-Infected Psyllids

The competence of F-ASOs in silencing bacterial genes inside *D. citri* was evaluated. A single F-ASO designed to target the CLas Ligase-A gene (CLIBASIA-1 (SEQ ID NO:22)) was used. The oligo was delivered to *D. citri* adults by feeding through the vascular system of excised citrus leaf disc which had taken up 300 µL of a 5 µM F-ASO solution. The scrambled control (AUM-C1-SC-1; SEQ ID NO:46) was used as a non-target control. A psyllid cohort was collected at seven days post-treatment, total RNA extracted from the psyllids and analyzed by qRT-PCR, using primers specific to the CLas Ligase-A gene. A cohort was analyzed at 10 days post feeding for presence of CLas infection.

Figure 15:
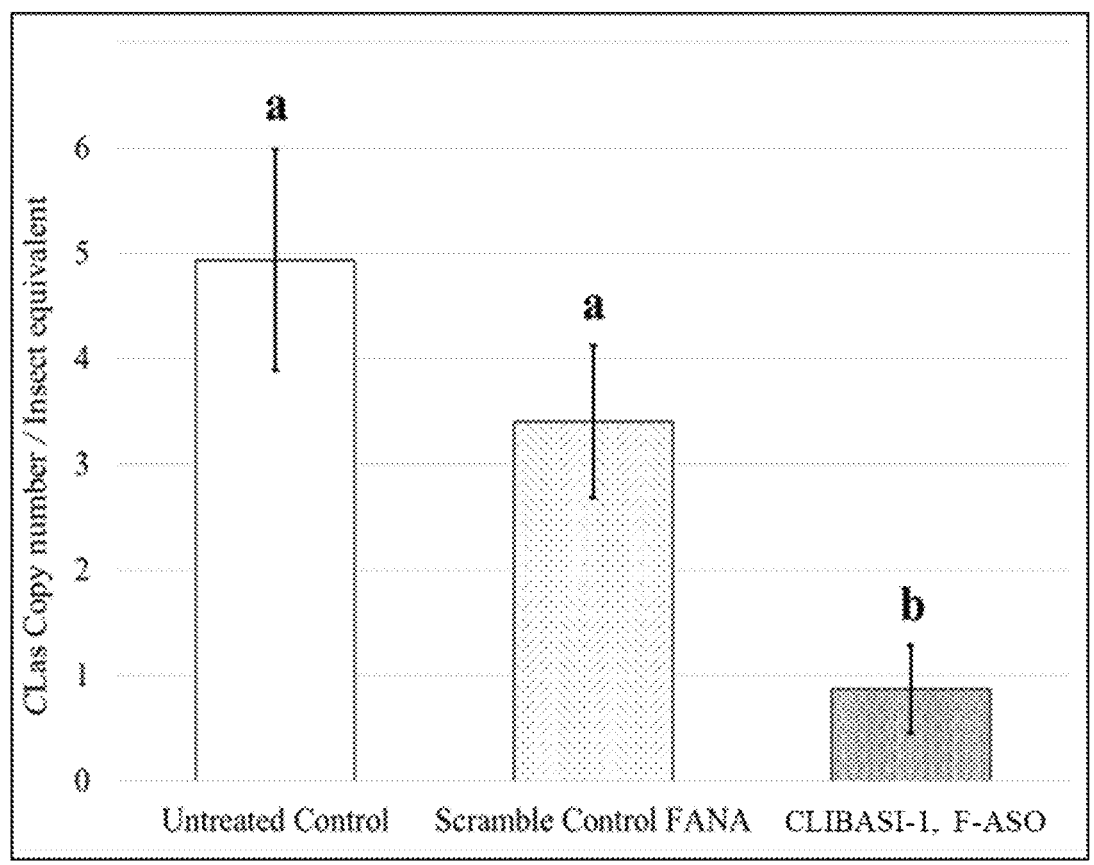

Feeding *D. citri* adults (16 adults, 8 male and 8 female) with F-ASO in artificial diet, in treated leaves, or in leaf discs from treated leaves contained in artificial conditions, significantly decreased the expression of the bacterial target gene by 75%, when compared to untreated psyllids [t (16)=−3.18, p=0.006] (representative results are shown in FIG. 15). The target transcript level was significantly lower in the psyllids exposed to the F-ASO treatment, compared to insects treated with the scramble control [t (13)=3.08, p=0.009]. There was no significant difference in the amount of CLas Ligase-A mRNA, between psyllids that were fed the scramble control SC-F-ASO nor the untreated control psyllids [t(13)=−0.007, p=0.99].

Figure 16:
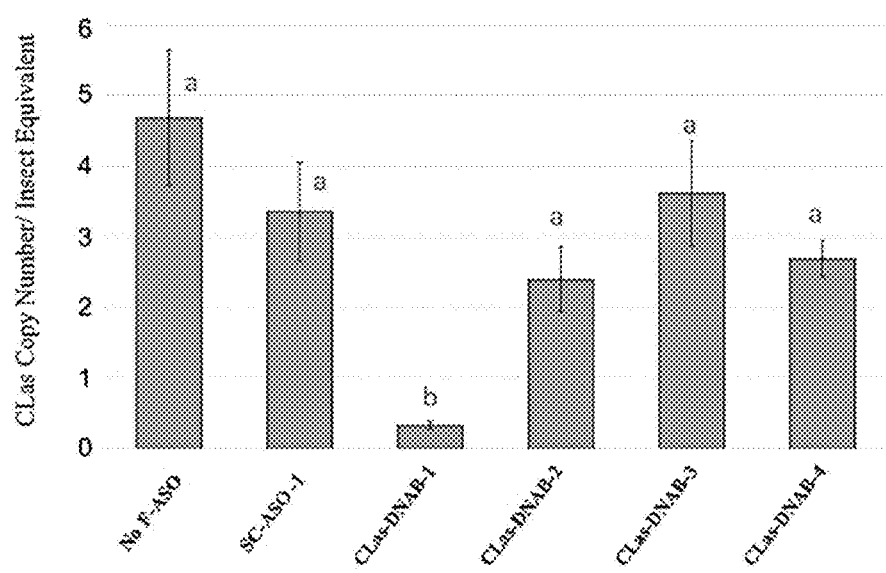

Sixteen adult psyllids (8 female/8 male) were provided feeding access to citrus tissue which was treated with 300 µL of a 5 µM F-ASO solution (CLASDNAB-1 (SEQ ID NO:4), CLASDNAB-2 (SEQ ID NO:5), CLASDNAB-3 (SEQ ID NO:6), or CLASDNAB-4 (SEQ ID NO:7)). The adult citrus psyllids were reared on CLas-infected citrus seedlings, collected and then provided feeding access to F-ASO treated citrus leaf tissue. The adult psyllids were validated to be CLas-infected at the end of the 10-day feeding access period with qPCR analyses. No significant differences were observed between the CLas titers in psyllids from the water blank or the scrambled control. Three of the F-ASOs were not significantly different in CLas genome copy numbers in psyllids: CLASDNAB-2 (SEQ ID NO:5) (0.48 CLas copy number), CLASDNAB-3 (SEQ ID NO:6) (2.37), and CLASDNAB-4 (SEQ ID NO:7) (3.7 log equivalents), compared to an average of 4.8 CLas equivalents in the non-treated infected controls. There was a significant reduction in CLas titers when feeding on CLasDNAB-1 treatment. The reduction of CLas represents a drop by 4.32 equivalents in CLas-infected psyllids which ingested the CLASDNAB-1 (SEQ ID NO:4) treatment. ANOVA: F (5, 48)=5.77, p=0.000. Tukey HSD test (P≤0.05). (FIG. 16).

CLas Acetyl-CoA Carboxylase Biotin Carboxylase Subunit (CLasBTIN) Target

Figure 17:
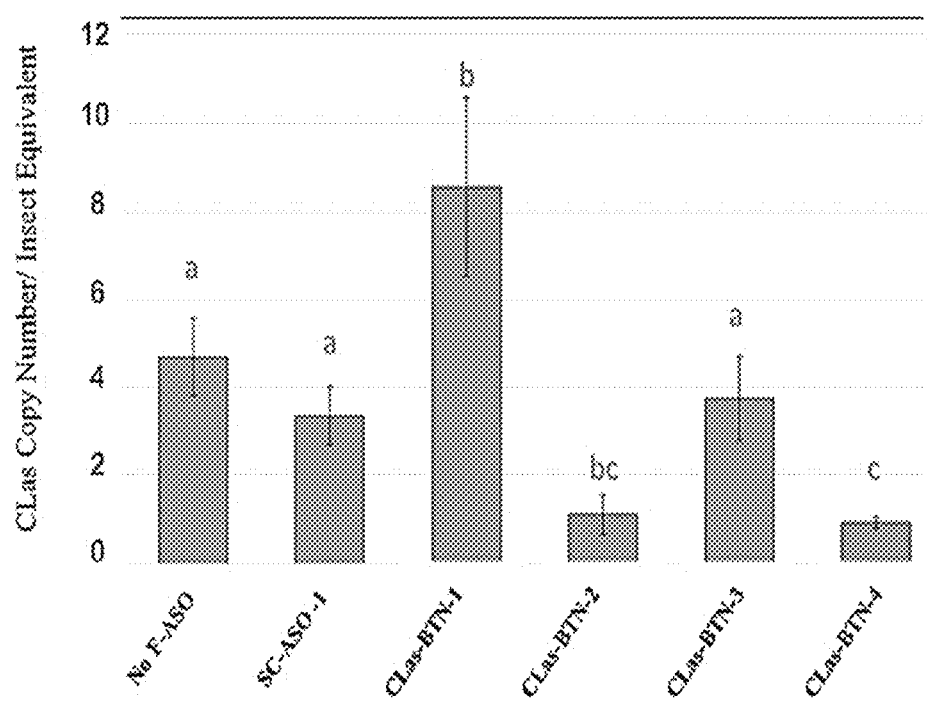

Sixteen CLas-infected adult *D. citri*, for each F-ASO, were giving feeding access for six days. The F-ASOs (CLASBTIN_1 (SEQ ID NO:34), CLASBTIN_2 (SEQ ID NO:35), CLASBTIN_3 (SEQ ID NO:36), or CLASBTIN_4 (SEQ ID NO:34)) were provided individually to adult psyllids in a citrus leaf disc which had taken up a 300 μL volume of a 5 μM F-ASO solution. Post ingestion, significant reduction was observed for psyllid fed CLASBTIN_2 (SEQ ID NO:35) and CLASBTIN_4 (SEQ ID NO:34) by 3.5- to 3.7-fold less respectively, compared to no treatment control (ANOVA: F (3, 32)=8.52, p=0.0003, LSD test (P≤0.05) (FIG. 17). There was no significant difference observed for CLASBTIN_3 (SEQ ID NO:36) treatments, and psyllids fed CLASBTIN_1 (SEQ ID NO:34) showed a significant increase in CLas titer by about 4.2-fold compared to both controls.

CLas DNA Ligase-A Target (Individual F-ASOs)

Figure 18:
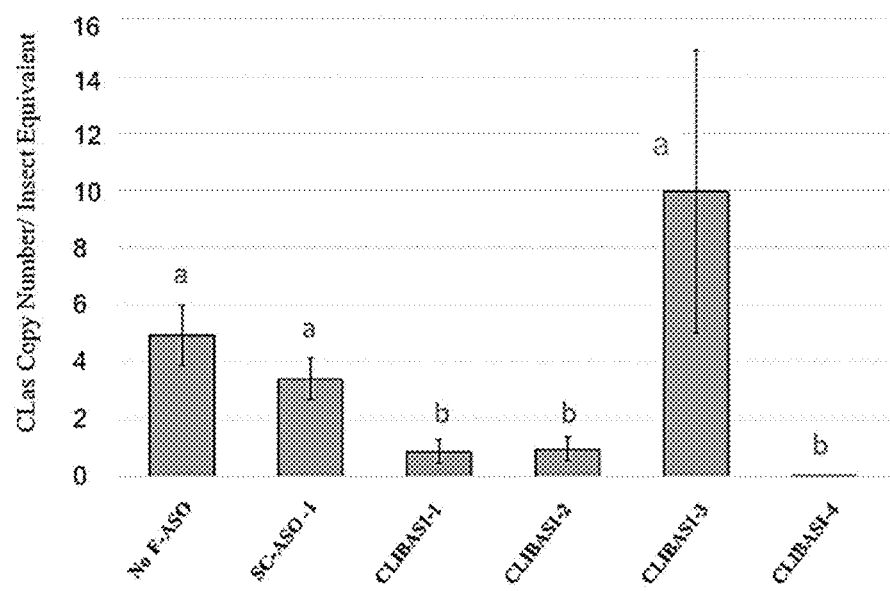

Sixteen CLas-infected adult *D. citri*, for each F-ASO, were giving feeding access to citrus leaf tissue for six days. Tissue uptake was accomplished by adding 3004, of 5 μM individual F-ASO solution (CLIBASIA-1 (SEQ ID NO:22), CLIBASIA-2 (SEQ ID NO:23), CLIBASIA-3 (SEQ ID NO:24), and CLIBASIA-4 (SEQ ID NO:25)). Post feeding, qPCR analysis revealed that three of the F-ASOs targeting the CLas DNA ligase-A (CLIBASIA-1 (SEQ ID NO:22), CLIBASIA-2 (SEQ ID NO:23), and CLIBASIA-3 (SEQ ID NO:24)) significantly reduced CLas copy numbers by 3.5 fold (CLIBASIA-1 and -2), and 4 fold (CLIBASIA-4) within CLas infected psyllids, compared to the control treatments (FIG. 18). CLIBASIA-3 showed no significant difference in CLas copy number compared to the controls (ANOVA: F (4, 40)=10.75, p≤0.0001, LSD test (P≤0.05).

Example 7

Controlling Insects Via F-ASO Feeding

Multiple F-ASOs to a Single Target (Syntaxin 1A) Applied as a Foliar Spray

Sweet orange citrus leaves were washed and rinsed with filtered water, with ends trimmed and placed into 150 mL flasks. When dry, the foliage was sprayed with a mixture containing 230.55 μg of each of the F-ASOs tested (DRW-SX1 (SEQ ID NO:38), DRW-SX2 (SEQ ID NO:39), DRW-SX3 (SEQ ID NO:40), and DRW-SX4 (SEQ ID NO:41)) (691.65 μg/5 mL per treatment), or in a combination of three of these F-ASOs (DRW-SX1 (SEQ ID NO:38), DRW-SX2 (SEQ ID NO:39), and DRW-SX3 (SEQ ID NO:40)). The treated cuttings were placed into cages 12"×12"×12", and then 11 female and 11 male adult weevils (*D. abbreviatus*) were added into each cage. Wax paper strips 2.5 cm wide and 16 cm long, two layers stapled together at the top end, were taped to the side of the cages to provide an oviposition substrate for egg laying. Each trial had four cages with 22 adult weevils and was repeated twice. Fresh leaves were provided each week. The fresh leaves for the F-ASO treatments were first sprayed with another application of the F-ASO solution. This was repeated for three weeks. Control received water sprays.

Figure 19:
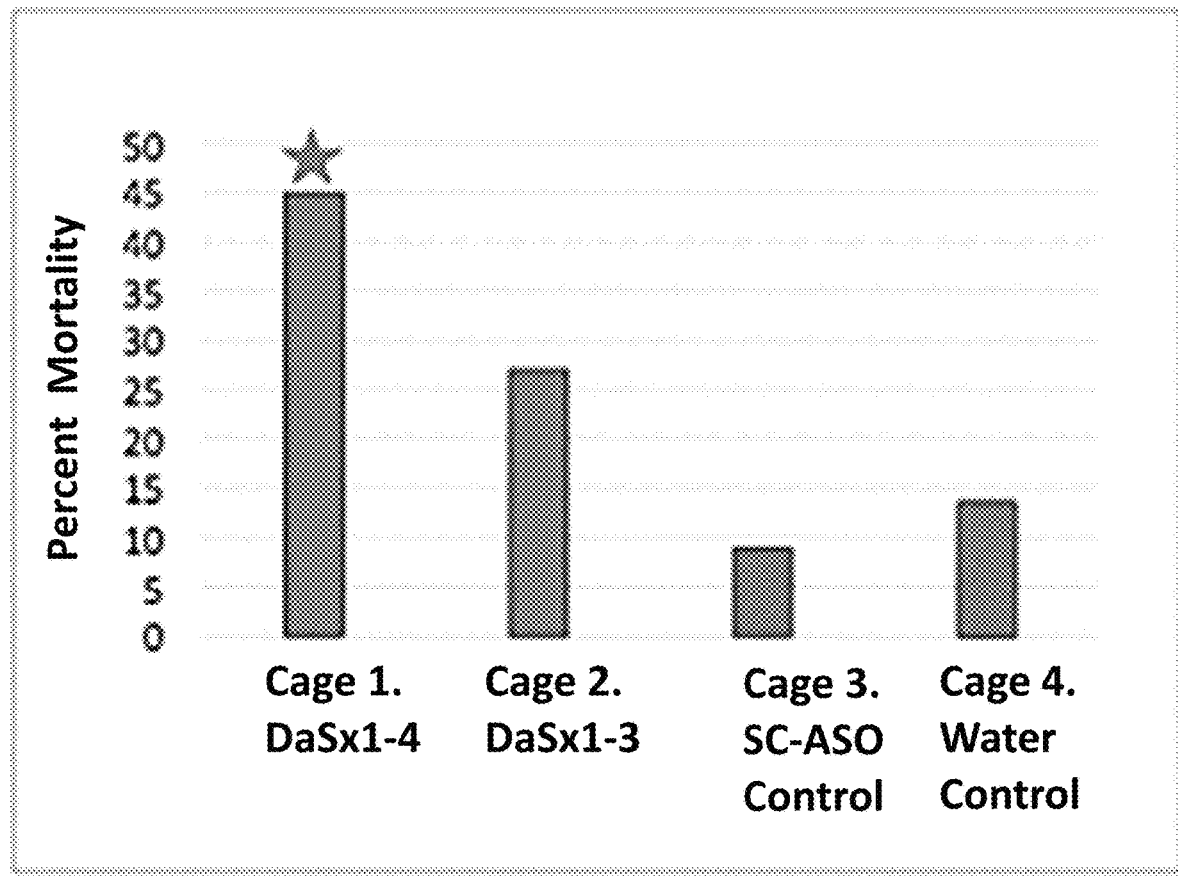

When the four F-ASO mixture (DRW-SX1 (SEQ ID NO:38), DRW-SX2 (SEQ ID NO:39), DRW-SX3 (SEQ ID NO:40), and DRW-SX4 (SEQ ID NO:41)) was applied, significant mortality of adults at 31 days post feeding was recorded. Comparison with the use of all four F-ASO versus just three (DRW-SX1 (SEQ ID NO:38), DRW-SX2 (SEQ ID NO:39), and DRW-SX3 (SEQ ID NO:40)) resulted in 45%, and 25.4% respectively, compared to the SC-ASO-3 (SEQ ID NO:3) scrambled control, which had 9.8% and the water blank controls with 14.5%. Results are shown in FIG. 19.

Individual F-ASOs to *D. abbreviatus* HSP90 Fed in Sugar Solution

Four F-ASOs were designed to *D. abbreviatus*, mRNA HSP90, heat shock protein 90. Experimental design included six treatment groups: no treatment control, scrambled control SC-ASO-3 (SEQ ID NO:3), and the four individual F-ASOs to HSP90 (Da90-1 (SEQ ID NO:42), Da90-2 (SEQ ID NO:43), Da90-3 (SEQ ID NO:44), and Da90-4 (SEQ ID NO:45)). Medium sized citrus leaves were placed into individual insect cages. 200 μL of sucrose solution (10% by wt) containing 133.2 μg of F-ASOs was pipetted onto each leaf. One female adult weevil was added to each feeding access cage. At 24 hours post feeding, weevils were transferred to group cages for each treatment which contained potted sweet orange seedling plants about 40 cm in height. Insect mortality was recorded over a 25-day period.

Figure 20:
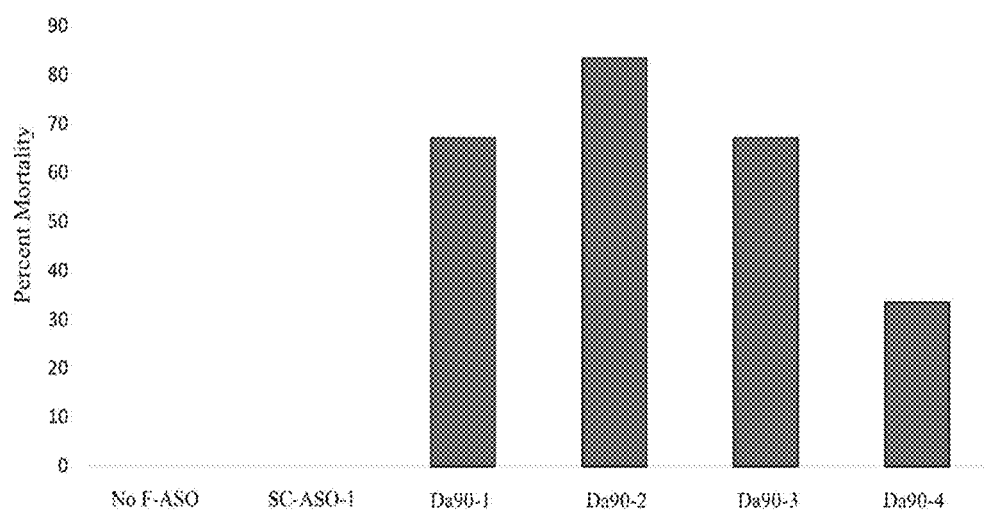

Behavioral differences such as slower walking and more standing still with one front leg raised were observed at 14 d post feeding of active F-ASOs. Weevils fed Da90-2 (SEQ ID NO:43) had delayed responses to disturbances and speed of ambulation was notably slower compared to both controls. Additionally, significant mortality was observed on day 25, at 66.7%, 83.3%, 66.7%, and 33.3% of mortality for Da90-1 (SEQ ID NO:42), Da90-2 (SEQ ID NO:43), Da90-3 (SEQ ID NO:44), and Da90-4 (SEQ ID NO:45), respectively (FIG. 20). No significant mortality was observed between the no treatment control and the scrambled control.

Individual F-ASOs to *D. citri* Post Ingestion with in Planta Bioassay

Figure 21:
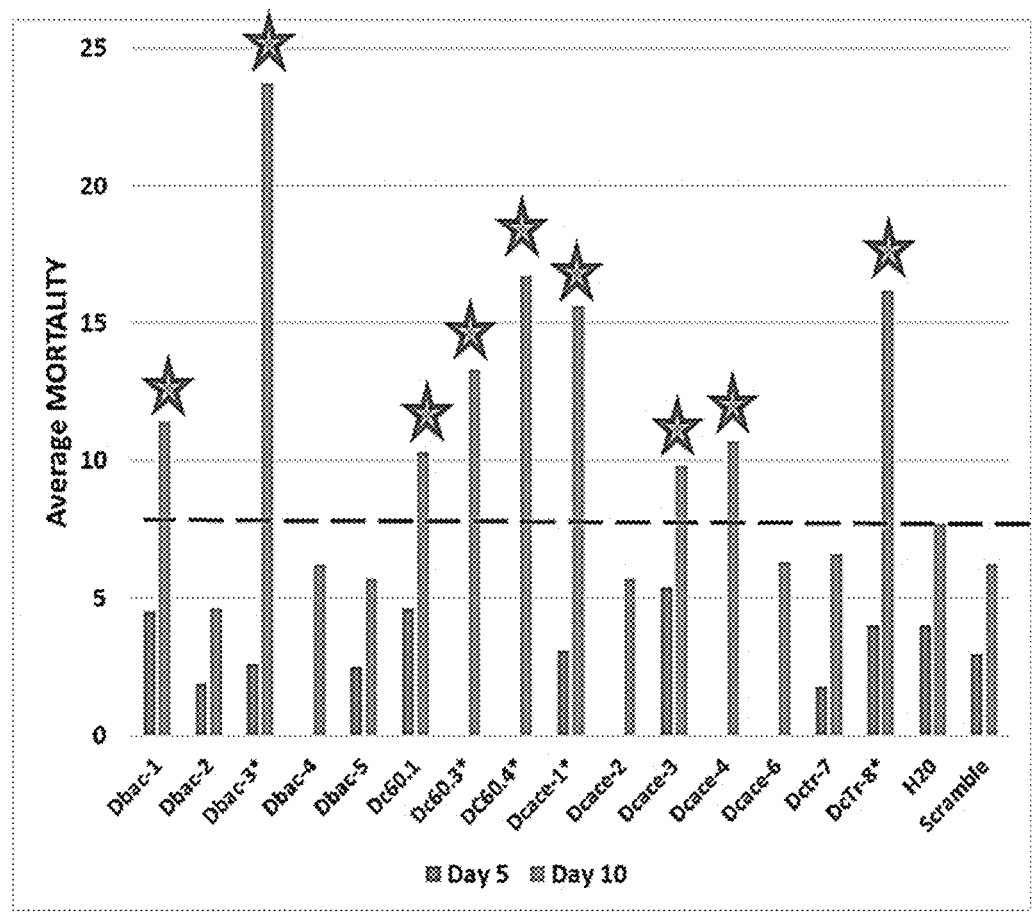

In planta feeding bioassay was utilized to test for effects on adult psyllid mortality following ingestion of F-ASO's. Feeding access period was 10 days on treated citrus cuttings and each treatment evaluated a single F-ASO (DBac-1 (SEQ ID NO:48), DBac-2 (SEQ ID NO:49), DBac-3 (SEQ ID NO:50), DBac-4 (SEQ ID NO:51), DBac-5 (SEQ ID NO:52), DCACE-1 (SEQ ID NO:53), DCACE-2 (SEQ ID NO:54), DCACE-3 (SEQ ID NO:55), DCACE-4 (SEQ ID NO:56), DCACE-6(SEQ ID NO:58); DC60-1 (SEQ ID NO:59), DC60-3 (SEQ ID NO:61), DcTR-7 (SEQ ID NO:68), and DcTR-8 (SEQ ID NO:69)). F-ASOs labeled "DBac" and "DCACE" target *D. citri* acetylcholine esterase transcripts, those labeled "Dc60" target *D. citri* 60S ribosomal protein, and those labeled "DcTr" target *D. citri* trehalase transcripts. Concentrations were normalized at 2.5 nmoles (22.5 μg) per 1 mL water absorbed by each citrus cutting which weighed between 0.5 to 0.65 of a gram. Each treatment had 6 cages with 20 adult psyllids per cage. Observations of mortality were collected on days 3, 5, and 10. Background mortality of control treatments ranged from 4% on day 5, to 10% on day 10. Nine F-ASO treatments had greater mortality than the controls SC-F-ASO, or water blank. Four of these resulted in a range of mortality from 12% to 20% above background. (FIG. 21).

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A method of inducing RNA silencing in a plant-chewing or phloem-feeding insect comprising the steps of:
   a. providing an oligonucleotide comprising at least one 2'F-ANA-modified nucleotide and at least one 2'-deoxyribonucleotide, and wherein the 2'F-ANA-modified nucleotides are positioned according to any of Formula 2-16, and having the sequence of SEQ ID NO: 39-46, SEQ ID NO: 48-69 and SEQ ID NO: 71-76 to the insect in a manner whereby the insect to ingests the oligonucleotide, thereby inducing RNA silencing.

2. The method of claim 1, wherein the insect ingests the oligonucleotide by consuming plant material containing the oligonucleotide.

3. The method of claim 1, wherein the insect is *Diaphorina citri* or *Diaprepes abbreviatus*.

4. The method of claim 1, wherein the plant is a citrus plant or a potato plant.

5. The method of claim 4, wherein plant is a citrus plant selected from the group consisting of orange, lemon, clementine, lime, grapefruit, pomelo, citron, mandarin, and tangelo.

6. The method of claim 1, comprising the additional step of applying the oligonucleotide to a plant.

7. The method of claim 6, wherein the oligonucleotide is applied to a plant by root soak, injection or foliar spray.

8. The method of claim 1, comprising the additional step of applying the oligonucleotide to an artificial diet, sugar solution or bait material.

9. A method of controlling a plant-chewing or phloem-feeding insect, comprising the steps of:
   a. providing an oligonucleotide comprising at least one 2'F-ANA-modified nucleotide and at least one 2'-deoxyribonucleotide, and wherein the 2'F-ANA-modified nucleotides are positioned according to any of Formula 2-16, and having a sequence selected from the group consisting of SEQ ID NO: 39-46, SEQ ID NO: 48-69 and SEQ ID NO: 71-76 in a manner whereby the insect to ingests the oligonucleotide, thereby inducing RNA silencing and a detrimental effect to the insect.

10. The method of claim 9, wherein the detrimental effect is increased mortality compared to insects not exposed to the oligonucleotide.

11. The method of claim 9, wherein the insect is *Diaphorina citri* or *Diaprepes abbreviatus*.

12. The method of claim 9, wherein the providing step comprises applying the oligonucleotide to a plant.

13. The method of claim 9, wherein the providing step comprises applying the oligonucleotide to an artificial diet, sugar solution or bait material.

14. A method of inducing RNA silencing in a *Diaphorina citri* or *Diaprepes abbreviatus* insect comprising the steps of:
   a. contacting *D. cirri* or *D. abbreviatus* with an oligonucleotide comprising at least one 2'F-ANA-modified nucleotide and at least one 2'-deoxyribonucleotide in an amount sufficient to induce RNA silencing, wherein the 2'F-ANA-modified nucleotides are positioned according to any of Formulas 2-16.

15. The method of claim 14, wherein the oligonucleotide is selected from the group consisting of SEQ ID NO: 39-46, SEQ ID NO: 48-69 and SEQ ID NO: 71-76.

16. The method of claim 14, wherein the insect is *D. citri* and the contacting comprises ingestion of phloem of a plant, wherein the phloem comprises the oligonucleotide.

17. The method of claim 14, wherein the insect is *D. abbreviatus* and the contacting comprises consumption of plant tissue, wherein the plant tissue comprises the oligonucleotide.

\* \* \* \* \*